(12) United States Patent
Weaver et al.

(10) Patent No.: US 7,501,429 B2
(45) Date of Patent: Mar. 10, 2009

(54) PYRIMIDINE COMPOUNDS AS ANTI-ICTOGENIC AND/OR ANTI-EPILEPTOGENIC AGENTS

(75) Inventors: Donald F. Weaver, Halifax (CA); Buhendwa Musole Guillain, Kingston (CA); John R. Carran, Kingston (CA); Kathryn Jones, Kingston (CA)

(73) Assignee: Queen's University at Kingston, Kingston, Ontario (CA)

(*) Notice: Subject to any disclaimer, the term of this patent is extended or adjusted under 35 U.S.C. 154(b) by 992 days.

(21) Appl. No.: 10/123,062

(22) Filed: Apr. 11, 2002

(65) Prior Publication Data

US 2003/0153584 A1  Aug. 14, 2003

Related U.S. Application Data

(63) Continuation of application No. 10/099,934, filed on Mar. 13, 2002.

(60) Provisional application No. 60/282,987, filed on Apr. 11, 2001, provisional application No. 60/285,940, filed on Apr. 23, 2001, provisional application No. 60/310,748, filed on Aug. 7, 2001.

(51) Int. Cl.
*A61K 31/513* (2006.01)
*C07D 239/10* (2006.01)

(52) U.S. Cl. .................. 514/269; 544/309

(58) Field of Classification Search .......... 514/269; 544/309–313
See application file for complete search history.

(56) References Cited

U.S. PATENT DOCUMENTS

| | | | | |
|---|---|---|---|---|
| 3,300,292 A | * | 1/1967 | Luckenbaugh | 504/243 |
| 4,171,439 A | * | 10/1979 | Menard et al. | 540/300 |
| 4,588,729 A | * | 5/1986 | Teranishi et al. | 514/269 |
| 4,625,028 A | * | 11/1986 | Smith | 544/309 |
| 4,649,142 A | * | 3/1987 | Takaya et al. | 514/274 |
| 4,950,670 A | * | 8/1990 | Frost et al. | 514/252.14 |
| 5,455,349 A | * | 10/1995 | Grasshoff et al. | 544/309 |
| 5,461,060 A | * | 10/1995 | Miyasaka et al. | 514/269 |
| 5,476,855 A | * | 12/1995 | el Kouni et al. | 514/269 |
| 5,721,241 A | * | 2/1998 | el Kouni et al. | 514/269 |
| 6,344,460 B1 | * | 2/2002 | Nirchio | 514/274 |
| 6,472,378 B2 | * | 10/2002 | von Borstel | 514/50 |
| 6,930,112 B2 | * | 8/2005 | Weaver et al. | 514/258.1 |

FOREIGN PATENT DOCUMENTS

| | | | |
|---|---|---|---|
| EP | 343050 A1 | * | 11/1989 |
| JP | 61-236724 | * | 10/1986 |
| WO | 99-51572 | * | 10/1999 |

OTHER PUBLICATIONS

Matsui et.al., J. Org. Chem., 1990, vol. 55, pp. 1396-1399.*
Baker et. al. J. Med. Chem., 1967, vol. 10, No. 3, pp. 316-320.*
Skulnick et. al., J. Med. Chem., 1986, vol. 29, pp. 1499-1504.*
Tateoka, Y. et. al., "Potentiating Effects of . . . -Diallyluracil, . . . Motor Incoordination." Chem. Pharm. Bull., Dec. 1987, vol. 35, No. 12, pp. 4928-4934.*
Gearien, J.E. et. al., "Synthesis of Analogs of Thymidine" J. Org. Chem., 1958, vol. 23, No. 3, pp. 491-492.*

* cited by examiner

*Primary Examiner*—James O Wilson
*Assistant Examiner*—Tamthom N Truong
(74) *Attorney, Agent, or Firm*—Carol Miernicki Steeg; Angela Lyon; Elizabeth A. Hanley

(57) ABSTRACT

Methods and compounds useful for the inhibition of convulsive disorders, including epilepsy, are disclosed. The methods and compounds of the invention inhibit or prevent ictogenesis and/or epileptogenesis. Methods for preparing the compounds of the invention are also described. Particularly preferred compounds of the invention include:

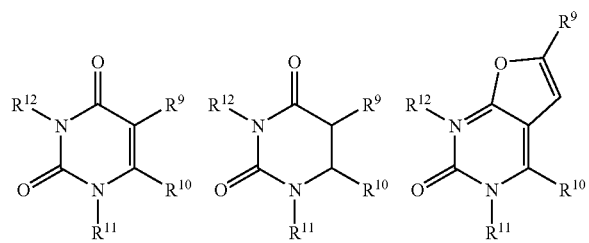

16 Claims, 2 Drawing Sheets

PYRIMIDINE COMPOUNDS AS ANTI-ICTOGENIC AND/OR ANTI-EPILEPTOGENIC AGENTS

RELATED APPLICATIONS

This application claims the priority of U.S. provisional patent application No. 60/282,987, filed Apr. 11, 2001, entitled "Anti-Epileptogenic Agents," U.S. provisional patent application No. 60/285,940, filed Apr. 23, 2001, entitled "Pyrimidine Compounds as Anti-Seizure Agents," and U.S. provisional patent application No. 60/310,748, filed Aug. 7, 2001, entitled "Pyrimidine Compounds as Anti-Ictogenic and/or Anti-Epileptogenic Agents," and U.S. patent application Ser. No. 10/099,934, filed Mar. 13, 2002, entitled "Anti-Epileptogenic Agents," the entire contents of each of which are incorporated herein by reference.

BACKGROUND OF THE INVENTION

Epilepsy is a serious neurological condition, associated with seizures, that affects hundreds of thousands of people worldwide. Clinically, a seizure results from a sudden electrical discharge from a collection of neurons in the brain. The resulting nerve cell activity is manifested by symptoms such as uncontrollable movements.

A seizure is a single discrete clinical event caused by an excessive electrical discharge from a collection of neurons through a process termed "ictogenesis." As such, a seizure is merely the symptom of epilepsy. Epilepsy is a dynamic and often progressive process characterized by an underlying sequence of pathological transformations whereby normal brain is altered, becoming susceptible to recurrent seizures through a process termed "epileptogenesis." While it is believed that ictogenesis and epileptogenesis have certain biochemical pathways in common, the two processes are not identical. Ictogenesis (the initiation and propagation of a seizure in time and space) is a rapid and definitive electrical/chemical event occurring over seconds or minutes. Epileptogenesis (the gradual process whereby normal brain is transformed into a state susceptible to spontaneous, episodic, time-limited, recurrent seizures, through the initiation and maturation of an "epileptogenic focus") is a slow biochemical and/or histological process which generally occurs over months to years. Epileptogenesis is a two phase process. Phase 1 epileptogenesis is the initiation of the epileptogenic process prior to the first seizure, and is often the result of stroke, disease (e.g., meningitis), or trauma, such as an accidental blow to the head or a surgical procedure performed on the brain. Phase 2 epileptogenesis refers to the process during which an individual already susceptible to seizures, becomes still more susceptible to seizures of increasing frequency and/or severity. While the processes involved in epileptogenesis have not been definitively identified, some researchers believe that upregulation of excitatory coupling between neurons, mediated by N-methyl-D-aspartate (NMDA) receptors, is involved. Other researchers implicate downregulation of inhibitory coupling between neurons, mediated by gamma-amino-butyric acid (GABA) receptors.

Although epileptic seizures are rarely fatal, large numbers of patients require medication to avoid the disruptive, and potentially dangerous, consequences of seizures. In many cases, medication is required for extended periods of time, and in some cases, a patient must continue to take prescription drugs for life. Furthermore, drugs used for the management of epilepsy have side effects associated with prolonged usage, and the cost of the drugs can be considerable.

A variety of drugs are available for the management of epileptic seizures, including older anticonvulsant agents such as phenytoin, valproate and carbamazepine (ion channel blockers), as well as newer agents like felbamate, gabapentin, and tiagabine. β-alanine has been reported to have anticonvulsant activity, as well as NMDA inhibitory activity and GABAergic stimulatory activity, but has not been employed clinically. Currently available accepted drugs for epilepsy are anticonvulsant agents, where the term "anticonvulsant" is synonymous with "anti-seizure" or "anti-ictogenic;" these drugs can suppress seizures by blocking ictogenesis, but it is believed that they do not influence epilepsy because they do not block epileptogenesis. Thus, despite the numerous drugs available for the treatment of epilepsy (i.e., through suppression of the convulsions associated with epileptic seizures), there are no generally accepted drugs for the treatment of the pathological changes which characterize epileptogenesis. There is no generally accepted method of inhibiting the epileptogenic process and there are no generally accepted drugs recognized as anti-epileptogenic.

SUMMARY OF THE INVENTION

This invention provides an anti-ictogenic and/or anti-epileptogenic compound of the formula (Formula XIV)

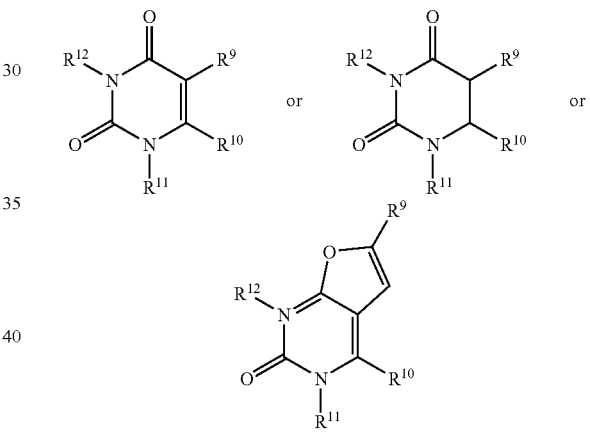

where $R^9$ is hydrogen, alkyl, alkynyl, hydroxy, halogen, nitro, carboxyl, or $R^9$ and $R^{10}$ together form a 5- or 6-membered carbocyclic or heterocyclic ring; $R^{10}$ is hydrogen, alkyl, carboxyl, or $R^9$ and $R^{10}$ together form a 5- or 6-membered carbocyclic or heterocyclic ring; $R^{11}$ is hydrogen or alkyl; and $R^{12}$ is hydrogen or alkyl; or pharmaceutically acceptable salts or esters (for example, of a hydroxyl or carboxyl group) thereof.

The invention also includes a pharmaceutical composition comprising any of the above compounds in combination with a pharmaceutically acceptable carrier. For example, the invention includes an anti-convulsive pharmaceutical composition including an amount of one or more of the above compounds effective to inhibit a convulsive disorder (e.g., epilepsy) in a subject in need thereof, and a pharmaceutically acceptable carrier.

In another aspect, this invention features a method of treating or preventing ictogenesis in a subject in need thereof including administering to the subject an amount of one or more of the above compounds to inhibit ictogenesis in the subject so that ictogenesis is treated or prevented in the subject.

In another aspect, this invention features a method of treating or preventing epileptogenesis in a subject in need thereof including administering to the subject an amount of one or more of the above compounds to inhibit epileptogenesis in the subject so that epileptogenesis is treated or prevented in the subject.

In addition, this invention provides a kit for treating or preventing ictogenesis in a subject including one of the above compounds, and instructions for administering a therapeutically effective amount of a compound to the subject so that ictogenesis is treated or prevented in the subject.

In addition, this invention provides a kit for treating or preventing epileptogenesis in a subject including one of the above compounds, and instructions for administering a therapeutically effective amount of a compound to the subject so that epileptogenesis is treated or prevented in the subject.

This invention further encompasses a method of diagnosing an epileptogenic condition in a subject including administering one of the above compounds labeled with a detectable marker to the subject; and measuring increased binding of the compound to the NMDA receptors of the neurons of the subject's brain so that an epileptogenic condition is diagnosed in the subject.

This invention further relates to a method of treating or preventing seizures in a subject suffering from head trauma including administering to the subject an amount of one of the above compounds so that seizures are treated or prevented in the subject.

DETAILED DESCRIPTION OF THE INVENTION

Figure 1:
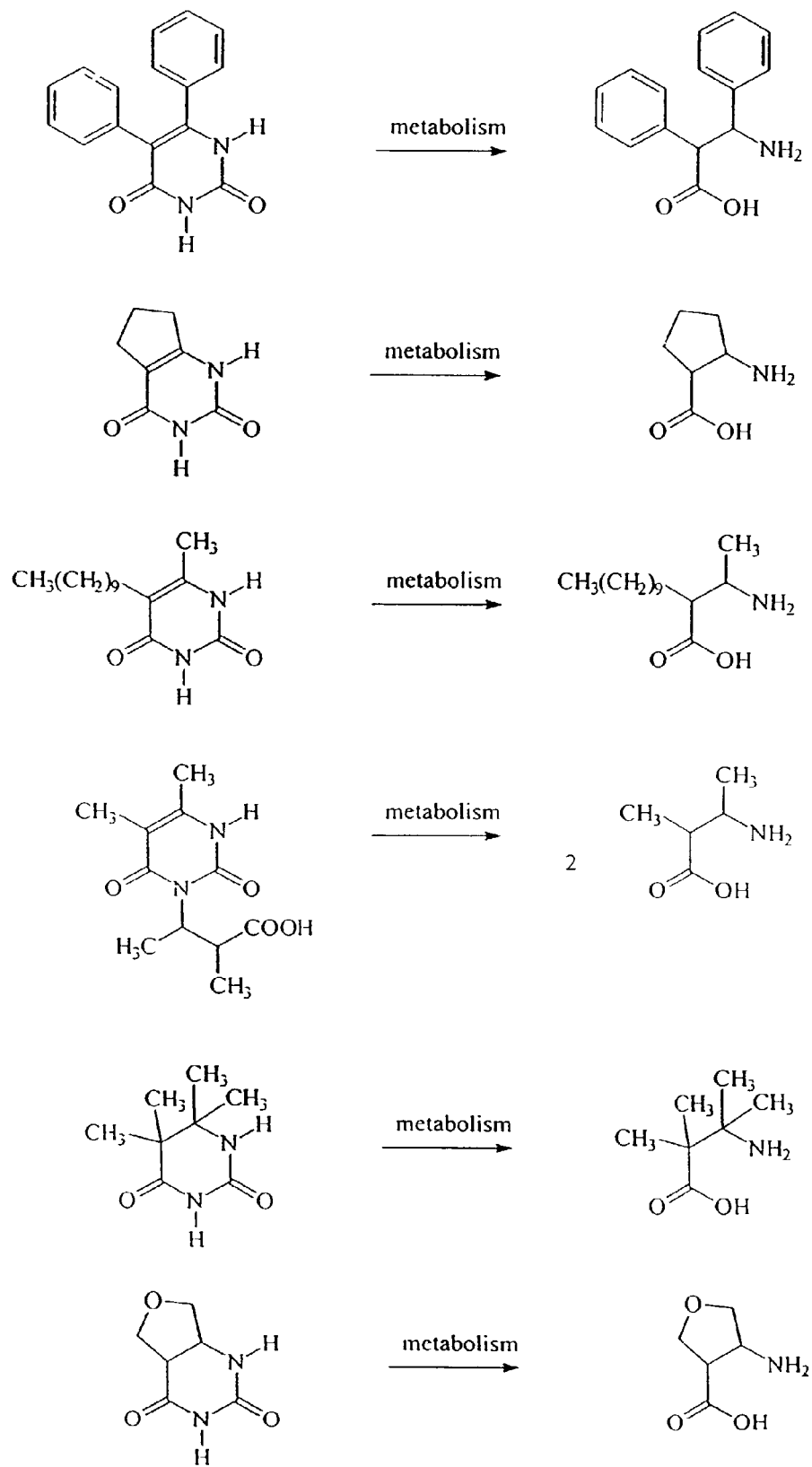
FIG. 1 depicts exemplary pyrimidine and dihydropyrimidine compounds useful in the methods of the invention and their putative metabolic conversion to β-amino acids.

This invention pertains to methods and agents useful for the treatment of epilepsy and convulsive disorders, for inhibition of epileptogenesis, and for inhibition of ictogenesis; and to methods for preparing anti-convulsive and anti-epileptogenic agents of the invention. The invention further pertains to pharmaceutical compositions for treatment of convulsive disorders, and to kits including the anti-convulsive compounds of the invention.

I. Definitions

For convenience, certain terms used in the specification, examples, and appended claims are collected here.

The language "a process in a pathway associated with epileptogenesis" includes biochemical processes or events which take place during Phase 1 or Phase 2 epileptogenesis and lead to epileptogenic changes in tissue, i.e., in tissues of the central nervous system (CNS), e.g., the brain. Examples of processes in pathways associated with epileptogenesis are discussed in more detail, infra.

The language "a disorder associated with NMDA receptor antagonism," includes disorders of a subject where abnormal (e.g., excessive) activity of NMDA receptors can be treated by antagonism of an NMDA receptor. Epilepsy is a disorder associated with excessive NMDA-mediated activity. Other non-limiting examples of disorders associated with excessive NMDA-mediated activity include pain, stroke, anxiety, schizophrenia, other psychoses, cerebral ischemia, Huntington's chorea, motor neuron disease, Alzheimer's disease, AIDS dementia and other disorders (in humans or animals) where excessive activity of NMDA receptors is a cause, at least in part, of the disorder. See, e.g., Schoepp et al., *Eur. J. Pharmacol.* 203:237-243 (1991); Leeson et al., *J. Med. Chem.* 34:1243-1252 (1991); Kulagowski et al., *J. Med. Chem.* 37:1402-1405 (1994); Mallamo et al., *J. Med. Chem.* 37:4438-4448 (1994); and references cited therein.

The term "convulsive disorder" includes disorders where the subject suffers from convulsions, e.g., convulsions due to epileptic seizure. Convulsive disorders include, but are not limited to, epilepsy and non-epileptic convulsions, e.g., convulsions due to administration of a convulsive agent to the subject.

The term "inhibition of epileptogenesis" includes preventing, slowing, halting, or reversing the process of epileptogenesis.

The term "anti-epileptogenic agent" includes agents which are capable of inhibiting epileptogenesis when the agent is administered to a subject.

The term "anticonvulsant agent" includes agents capable of inhibiting (e.g., preventing, slowing, halting, or reversing) ictogenesis when the agent is administered to a subject.

The term "pharmacophore" is known in the art, and includes molecular moieties capable of exerting a selected biochemical effect, e.g., inhibition of an enzyme, binding to a receptor, chelation of an ion, and the like. A selected pharmacophore can have more than one biochemical effect, e.g., can be an inhibitor of one enzyme and an agonist of a second enzyme. A therapeutic agent can include one or more pharmacophores, which can have the same or different biochemical activities. The skilled practitioner will recognize that a number of pharmacophores with similar structures and/or properties (e.g., biological effects) may be combined to predict or design an optimized or "average pharmacophore" structure. Such an average pharmacophore structure may provide a more desired level of biological effect than the individual pharmacophores used to create the average structure.

An "anionic group" refers to a group that is negatively charged at physiological pH. Preferred anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups include bioisosteres, e.g., bioisosteres of a carboxylate group. Bioisosteres encompass both classical bioisosteric equivalents and non-classical bioisosteric equivalents. Classical and non-classical bioisosteres are known in the art. See, e.g., Silverman, R. B. *The Organic Chemistry of Drug Design and Drug Action*, Academic Press, Inc.: San Diego, Calif., 1992, pp. 19-23. A particularly preferred anionic group is a carboxylate.

The term "β-amino anionic compound" includes compounds having an amino group, such as —NR$^a$R$^b$, where R$^a$ and R$^b$ may each independently be hydrogen, alkyl, alkenyl, alkynyl, cycloalkyl, aryl, alkylcarbonyl, arylcarbonyl, alkoxycarbonyl, or aryloxycarbonyl, or R$^a$ and R$^b$, taken together with the nitrogen atom to which they are attached, form a cyclic moiety having from 3 to 8 atoms in the ring separated from an anionic group by a two-carbon spacer unit. Thus, for example, a β-amino anionic compound can be represented by the substructural formula A-C—C—NR$^a$R$^b$, where A is an anionic group. Preferred β-amino anionic compounds include β-amino acids and analogs thereof. In certain preferred embodiments, the β-amino anionic compound is not β-alanine or taurine.

The term "subject" is known in the art, and refers to a warm-blooded animal, more preferably a mammal, including non-human animals such as rats, mice, cats, dogs, sheep, horses, cattle, in addition to apes, monkeys, and humans. In a preferred embodiment, the subject is a human.

Unless specifically indicated, the chemical groups of the present invention may be substituted or unsubstituted. Further, unless specifically indicated, the chemical substituents may in turn be substituted or unsubstituted. In addition, multiple substituents may be present on a chemical group or substituent. Examples of substituents include alkyl, alkenyl, alkynyl, aryl, halogen, hydroxyl, alkylcarbonyloxy, arylcarbonyloxy, alkoxycarbonyloxy, aryloxycarbonyloxy, carboxyl, alkylcarbonyl, arylcarbonyl, alkoxycarbonyl, aminocarbonyl, alkylaminocarbonyl, dialkylaminocarbonyl, alkylthiocarbonyl, alkoxyl, formyl, trimethylsilyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amido, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, and aromatic or heteroaromatic moieties.

The term "alkyl" refers to saturated aliphatic groups, including straight-chain alkyl groups, branched-chain alkyl groups, cycloalkyl, heterocyclyl, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably has 20 or fewer carbon atoms in the backbone. Likewise, preferred cycloalkyls have from 4-10 carbon atoms in their ring structure, and more preferably have 5, 6 or 7 carbons in the ring structure.

Moreover, alkyl (e.g., methyl, ethyl, propyl, butyl, pentyl, hexyl, etc.) include both "unsubstituted alkyl" and "substituted alkyl", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (i.e., benzyl)).

The term "aryl" includes 5- and 6-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring (e.g., phenyl, indole, thiophene) can be substituted at one or more ring positions with such substituents as described above, as for example, halogen, hydroxyl, alkylcarbonyloxy, arylcarbonyloxy, alkoxycarbonyloxy, aryloxy-carbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Aryl groups can also be fused or bridged with alicyclic or heterocyclic rings which are not aromatic so as to form a polycycle such as tetralin.

The terms "alkenyl" and "alkynyl" include unsaturated aliphatic groups analogous in length and possible substitution to the alkyls described above, but that contain at least one double or triple bond respectively and at least two adjacent carbon atoms.

As used in the description and drawings herein, an "optional single/double bond" is represented by a solid line together with a dashed line, and refers to a covalent linkage between two carbon atoms which can be either a single bond or a double bond of either E- or Z-configuration where appropriate. For example, the structure:

can represent either cyclohexane or cyclohexene.

Unless the number of carbons is otherwise specified, "lower alkyl" means an alkyl group as defined above, but having from one to ten carbons, more preferably from one to six carbon atoms in its backbone structure. Likewise, "lower alkenyl" and "lower alkynyl" have similar chain lengths (and at least two carbon atoms). Preferred alkyl groups are lower alkyls.

The terms "heterocyclyl" or "heterocyclic group" refer to 3- to 10-membered ring structures, more preferably 4- to 7-membered rings, which ring structures include one or more heteroatoms, e.g., two, three, or four. Heterocyclyl groups include pyrrolidine, oxolane, thiolane, piperidine, piperazine, morpholine, lactones, lactams such as azetidinones and is pyrrolidinones, sultams, sultones, and the like. The heterocyclic ring can be substituted at one or more positions with such substituents as described above, including halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety.

The terms "polycyclyl" or "polycyclic group" refer to two or more cyclic rings (e.g., cycloalkyls, cycloalkenyls, cycloalkynyls, aryls and/or heterocyclyls) where two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety.

The term "heteroatom" as used herein means an atom of any element other than carbon or hydrogen. Preferred heteroatoms are nitrogen, oxygen, sulfur and phosphorus.

The term "aryl aldehyde," as used herein, refers to a compound represented by the formula Ar—C(O)H, where Ar is an aryl moiety (as described above) and —C(O)H is a formyl or aldehydo group. In a preferred embodiment, the aryl aldehyde is a (substituted or unsubstituted) benzaldehyde. A variety of aryl aldehydes are commercially available, or can be prepared by routine procedures from commercially available precursors. Procedures for the preparation of aryl aldehydes include the Vilsmeier-Haack reaction (See, e.g., Jutz, *Adv. Org. Chem.* 9, pt. 1, 225-342 (1976)), the Gatterman reaction (Truce, *Org. React.* 9, 37-72 (1957)), the Gatterman-Koch reaction (Crounse, *Org. React.* 5, 290-300 (1949)), and the Reimer-Tiemann reaction (Wynberg and Meijer, *Org. React.* 28, 1-36 (1982)).

It will be noted that the structure of some of the compounds of this invention includes asymmetric carbon atoms. It is to be understood accordingly that the isomers arising from such asymmetry (e.g., all enantiomers and diastereomers) are included within the scope of this invention unless indicated otherwise. Such isomers can be obtained in substantially pure form by classical separation techniques and by stereochemically controlled synthesis. That is, unless otherwise stipulated, any chiral carbon center may be of either (R)- or (S)- stereochemistry. Furthermore, alkenes can include either the E- or Z-geometry, where appropriate.

Furthermore, one skilled in the art will appreciate that the chemical structures as drawn may represent a number of possible tautomers, and the present invention includes those tautomers.

II. Methods for Treating Convulsive Disorders

In one aspect, the invention provides methods for treating convulsive disorders, including epilepsy.

In one aspect, the invention provides a method for inhibiting epileptogenesis in a subject. The method includes administering to a subject in need thereof an effective amount of an agent which modulates a process in a pathway associated with epileptogenesis such that epileptogenesis is inhibited in the subject.

As noted above, upregulation of excitatory coupling between neurons, mediated by N-methyl-D-aspartate (NMDA) receptors, and downregulation of inhibitory coupling between neurons, mediated by gamma-amino-butyric acid (GABA) receptors, have both been implicated in epileptogenesis. Other processes in pathways associated with epileptogenesis include release of nitric oxide (NO), a neurotransmitter implicated in epileptogenesis; release of calcium ($Ca^{2+}$), which may mediate damage to neurons when released in excess; neurotoxicity due to excess zinc ($Zn^{2+}$); neurotoxicity due to excess iron ($Fe^{2+}$); and neurotoxicity due to oxidative cell damage. Accordingly, in preferred embodiments, an agent to be administered to a subject to inhibit epileptogenesis preferably is capable of inhibiting one or more processes in at least one pathway associated with epileptogenesis. For example, an agent useful for inhibition of epileptogenesis can reduce the release of, or attenuate the epileptogenic effect of, NO in brain tissue; antagonize an NMDA receptor; augment endogenous GABA inhibition; block voltage-gated ion channels; reduce the release of, reduce the free concentration of (e.g., by chelation), or otherwise reduce the epileptogenic effect of cations including $Ca^{2+}$, $Zn^{2+}$, or $Fe^{2+}$; inhibit oxidative cell damage; or the like. In certain preferred embodiments, an agent to be administered to a subject to inhibit epileptogenesis is capable of inhibiting at least two processes in at least one pathway associated with epileptogenesis.

Non-limiting examples of pharmacophores which can modulate a process in a pathway associated with epileptogenesis include:

inhibitors of NO synthase such as L-arginine and alkylated derivatives thereof;

antagonists of NMDA receptors such as (R)-α-amino acids. See, e.g., Leeson, P. D. and Iverson, L. L., *J. Med. Chem.* (1994) 37:4053-4067 for a general review of inhibitors of the NMDA receptor;

augmenters of endogenous GABA inhibition such as inactivators of GABA aminotransferase like gamma-vinyl-GABA. See, e.g., Krogsgaard-Larsen, P., et al., *J. Med. Chem.* (1994) 37:2489-2505) for a review of GABA receptor agonists and antagonists;

chelators of $Ca^{2+}$, $Zn^{2+}$, or $Fe^{2+}$ such as EDTA, EGTA, TNTA, 2,2-bipyridine-4,4,-dicarboxylate, enterobactin, porphyrins, crown ethers, and azacrown ethers; and antioxidants such as vitamins C, and E; carotenoids such as β-carotene; butylated phenols, Trolox (a tocopherol analog), selenium; and glutathione.

In one preferred embodiment, the agent antagonizes an NMDA receptor and augments endogenous GABA inhibition. In certain preferred embodiments, the agent is administered orally. Preferably, after oral administration, the agent is transported to the nervous system of the subject by an active transport shuttle mechanism. A non-limiting example of an active transport shuttle is the large neutral amino acid transporter, which is capable of transporting amino acids across the blood-brain barrier (BBB).

The step of administering to the subject can include administering to the subject a compound which is metabolized to an anti-convulsant and/or anti-epileptogenic compound of the invention. For example, the methods of the invention include the use of prodrugs which are converted in vivo to the therapeutic compounds of the invention. See, e.g., Silverman, ch. 8, cited above. Such prodrugs can be used to alter the biodistribution to allow compounds which would not typically cross the blood-brain barrier to cross the blood-brain barrier, or the pharmacokinetics of the therapeutic compound. For example, an anionic group, e.g., a carboxylate group, can be esterified with an ethyl or a fatty group to yield a carboxylic ester. When the carboxylic ester is administered to a subject, the ester can be cleaved, enzymatically or non-enzymatically, to reveal the anionic group.

In another illustrative embodiment, the methods of the invention include administering to the subject a derivative of uracil or an analog thereof (including substituted pyrimidines, UMP and uridine, or analogs thereof). Administration of a uracil compound or metabolite thereof, such as a dihydrouracil or a β-ureidopropionate, can result in the in vivo formation of an active compound of the invention. Accordingly, in a preferred embodiment, the methods of the invention may include the step of administering to a subject in need thereof an effective amount of a substituted or unsubstituted uracil, dihydrouracil or β-ureidopropionate compound, or a derivative or analog thereof (or a pharmaceutically acceptable salt or ester thereof), in an amount effective to treat a convulsive disorder and/or to inhibit epileptogenesis, e.g., by in vivo conversion of the uracil, dihydrouracil or β-ureidopropionate compound to a β-amino acid compound effective to treat the convulsive disorder.

Thus, in certain embodiments, preferred compounds for administration to a subject include pyrimidines such as substituted uracils which can be converted in vivo to β-amino anionic compounds. In a preferred embodiment, the compound can be represented by the formula (Formula V):

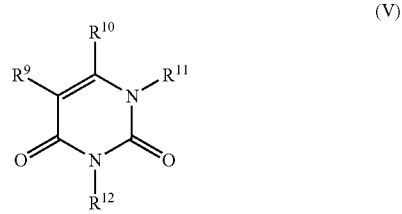

where $R^9$ and $R^{10}$ may each independently be hydrogen, alkyl (including cycloalkyl, heterocyclyl, and aralkyl), alkenyl, alkynyl, aryl, alkoxy, aryloxy, alkylcarbonyl, arylcarbonyl, alkoxycarbonyl, aryloxycarbonyl, amino (including unsubstituted and substituted amino), hydroxy, thiol, alkylthiol, nitro, cyano, halogen, carboxyl, alkoxycarbonyloxy, aryloxycarbonyloxy or aminocarbonyl; or $R^9$ and $R^{10}$, together with the two-carbon unit to which they are attached, are joined to form a carbocyclic or heterocyclic ring having from 4 to 8 members in the ring; and $R^{11}$ is hydrogen, alkyl, alkenyl, alkynyl, cycloalkyl, aryl, alkylcarbonyl, arylcarbonyl, alkoxycarbonyl, or aryloxycarbonyl; or $R^{10}$ and $R^{11}$, together with the carbon atom and nitrogen atom to which they are respectively attached, are joined to form a heterocyclic ring having from 4 to 8 members in the ring; and $R^{12}$ is selected from the group consisting of hydrogen, alkyl, aryl and a carbohydrate (such as a sugar, e.g., ribose or deoxyribose); or a pharmaceutically acceptable salt or ester thereof. In another embodiment, the compound can be represented by the formula (Formula Va):

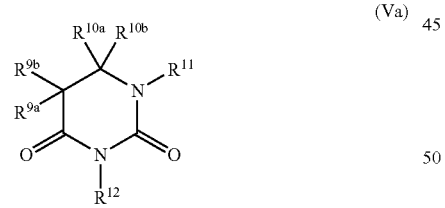

where $R^{9a}$, $R^{9b}$, $R^{10a}$, $R^{10b}$ may each independently be hydrogen, alkyl (including cycloalkyl, heterocyclyl, and aralkyl), alkenyl, alkynyl, aryl, alkoxy, aryloxy, alkylcarbonyl, arylcarbonyl, alkoxycarbonyl, aryloxycarbonyl, amino (including unsubstituted and substituted amino), hydroxy, thiol, alkylthiol, nitro, cyano, halogen, carboxyl, alkoxycarbonyloxy, aryloxycarbonyloxy or aminocarbonyl; or $R^{9a}$ and $R^{9b}$, together with the two-carbon unit to which they are attached, are joined to form a carbocyclic or heterocyclic ring having from 4 to 8 members in the ring; or $R^{10a}$ and $R^{10b}$, together with the two-carbon unit to which they are attached, are joined to form a carbocyclic or heterocyclic ring having from 4 to 8 members in the ring; or one of $R^{9a}$ and $R^{9b}$ is joined with one of $R^{10a}$ and $R^{10b}$, together with the two-carbon unit to which they are attached, to form a carbocyclic or heterocyclic ring having from 4 to 8 members in the ring; $R^{11}$ is hydrogen, alkyl, alkenyl, alkynyl, cycloalkyl, aryl, alkylcarbonyl, arylcarbonyl, alkoxycarbonyl, or aryloxycarbonyl; or one of $R^{10b}$ and $R^{10b}$ is joined with $R^{11}$, together with the carbon atom and nitrogen atom to which they are respectively attached, to form a heterocyclic ring having from 4 to 8 members in the ring; and $R^{12}$ is selected from the group consisting of hydrogen, alkyl, aryl and a carbohydrate (such as a sugar, e.g., ribose or deoxyribose); or a pharmaceutically acceptable salt or ester thereof.

A preferred group of compounds according to the invention include

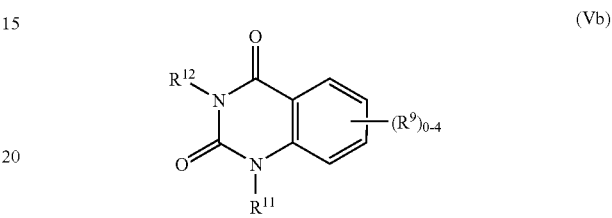

where $R^9$ (each selected independently of other $R^9$ groups, if any), $R^{11}$, and $R^{12}$ are defined above.

Another preferred group of compounds include

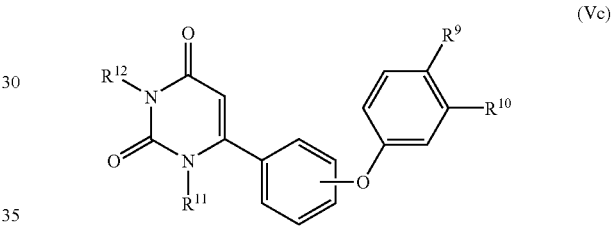

where $R^9$, $R^{10}$, $R^{11}$, and $R^{12}$ are defined above. More preferred are the following compounds

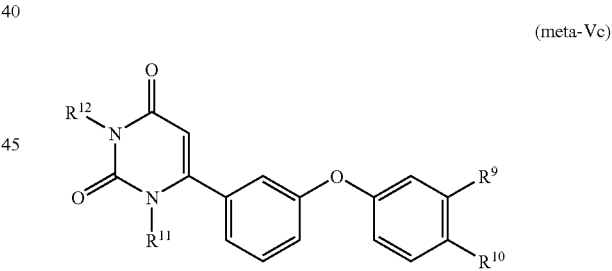

where $R^9$, $R^{10}$, $R^{11}$, and $R^{12}$ are defined above.

Still another preferred group of compounds include

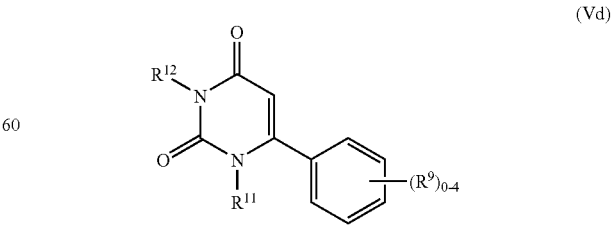

where $R^9$ (each selected independently of other $R^9$ groups, if any), $R^{11}$, and $R^{12}$ are defined above.

Also within the scope of the invention are the corresponding dihydrouracil compounds:

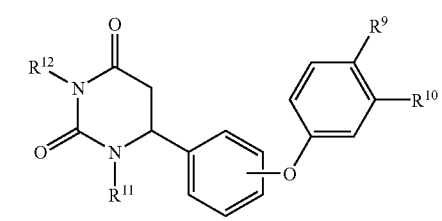
(Ve)

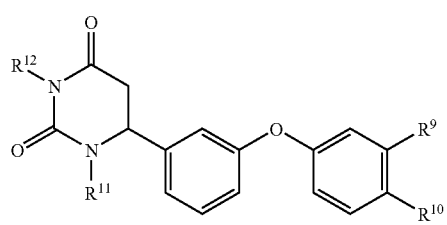
(meta-Ve)

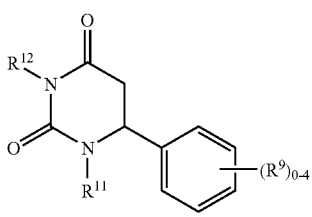
(Vf)

where $R^9$ (each selected independently of other $R^9$ groups, if any), $R^{10}$, $R^{11}$, and $R^{12}$ are defined above, and including all possible stereoisomers.

Pyrimidine compounds, such as 5-fluorouracil (5FU), have been used as anti-neoplastic agents. The anti-cancer activity of 5FU and similar compounds is believed to be due to a "suicide substrate" mechanism where the 5FU inhibits thymidylate synthase, an enzyme important in DNA synthesis. In preferred embodiments, pyrimidine and dihydropyrimidine compounds administered according to the invention for the treatment of convulsive disorders (inhibition of epileptogenesis) do not significantly inhibit thymidylate synthase. Without wishing to be bound by theory, it is believed that inhibition of thymidylate synthase by pyrimidine compounds is increased by the presence of electronegative groups at the 5-position of the pyrimidine ring (i.e., $R^9$ of Formula 5), and can therefore be decreased by providing such compounds with non-electronegative groups at the 5-position of the pyrimidine ring (i.e., $R^9$ of Formula 5). It is further believed that by providing substituents with sufficient steric bulk to decrease the ability of the pyrimidine compound to bind to thymidylate synthase, inhibition of thymidylate synthase can be decreased. Thus, in preferred embodiments, in a compound of Formula V for administration according to the present invention, $R^9$ is a non-electronegative (i.e., neutral or electropositive) group (e.g., alkyl, aryl, or the like). In preferred embodiments, at least one of $R^9$ and $R^{10}$ of Formula V is a sterically bulky group (e.g., long-chain or branched alkyl, substituted aryl, or the like), or $R^9$ and $R^{10}$ are joined to form a carbocyclic or heterocyclic ring.

Non-limiting examples of pyrimidine and dihydropyrimidine compounds for use according to the invention, together with illustrative active metabolites thereof, are shown in FIG. 1.

As illustrated in FIG. 1, the β-alanine, uracils, and dihydrouracils are metabolically related. Accordingly, uracil and dihydrouracil compounds which are analogous to β-alanines are within the scope of the present invention including, for example, the following:

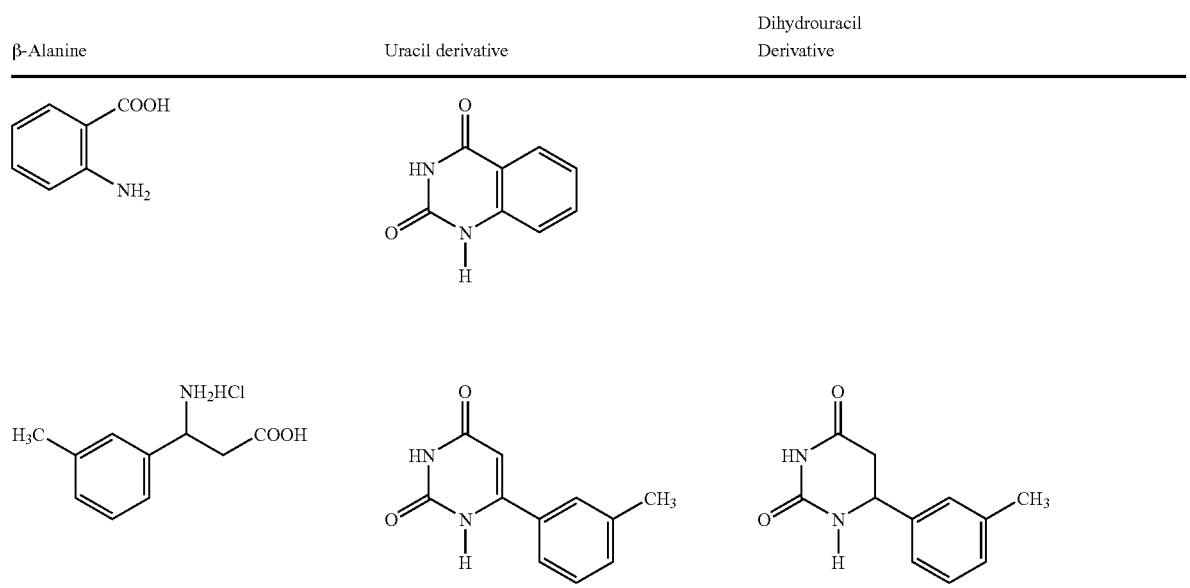

| β-Alanine | Uracil derivative | Dihydrouracil Derivative |
|---|---|---|

-continued

| β-Alanine | Uracil derivative | Dihydrouracil Derivative |
|---|---|---|

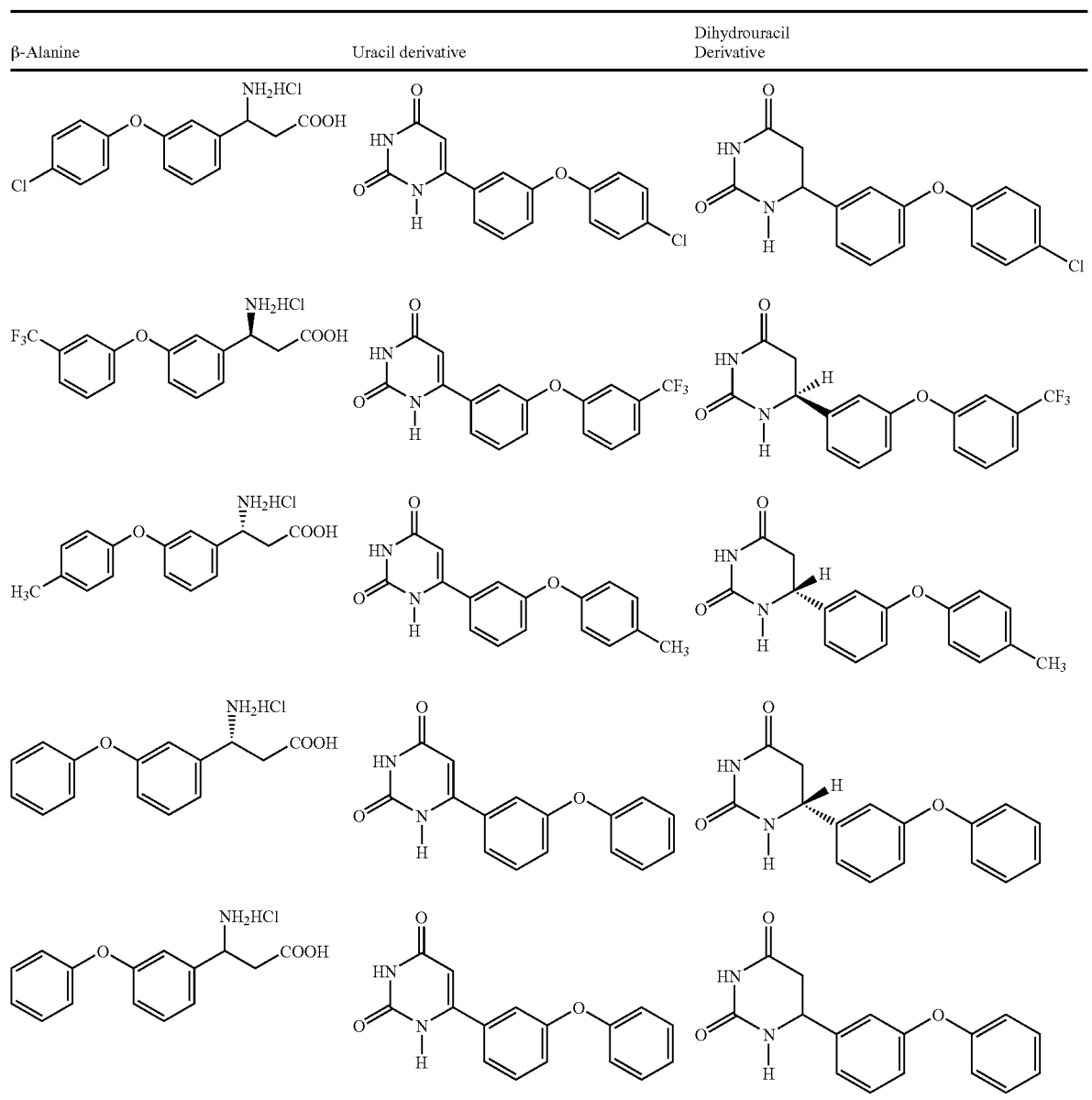

The use of substituted or unsubstituted uracils, and derivatives or analogs thereof, may be especially advantageous as certain uracil compounds have been found to have anti-ictogenic properties (only) when tested in an anti-seizure model in rats. See, eg *Medicinal Chemistry* Volume V; W. J. Close, L. Doub, M. A. Spielman; Editor W. H. Hartung; John Wiley and Sons (1961). Thus, the prodrug form of the compound (a uracil) can have anti-seizure activity, while the metabolically-produced β-amino anionic compounds can have anti-epileptogenic and/or anti-convulsive activity. These activities, individually and in combination, can provide effective therapy for convulsive disorders in mammals (including humans).

In certain embodiments, an active agent of the invention antagonizes NMDA receptors by binding to the glycine binding site of the NMDA receptors. In certain preferred embodiments, the agent augments GABA inhibition by decreasing glial GABA uptake. In certain other embodiments, the agent is administered orally. In yet other embodiments, the method further includes administering the agent in a pharmaceutically acceptable vehicle.

In another embodiment, the invention provides a method for inhibiting both a convulsive disorder and epileptogenesis in a subject. The method includes the step of administering to a subject in need thereof an effective amount of an agent which a) blocks sodium or calcium ion channels, or opens potassium or chloride ion channels; and b) has at least one activity selected from the group consisting of NMDA receptor antagonism; augmentation of endogenous GABA inhibition; calcium binding; iron binding; zinc binding; NO synthase inhibition; and antioxidant activity; such that epileptogenesis is inhibited in the subject.

Blockers of sodium and/or calcium ion channel activity are well known in the art and can be used as the A moiety (as described hereinbelow in the context of bifunctional molecules) in the compounds and methods of the present invention. Similarly, any compound which opens potassium or chloride ion channels can be used as the A moiety in the compounds and methods of the present invention. Antagonists of NMDA receptors and augmenters of endogenous GABA inhibition are also known to one of skill in the art and can be used in the methods and compounds of the invention. For example, 2,3-quinoxalinediones are reported to have NMDA receptor antagonistic activity (See, e.g., U.S. Pat. No. 5,721,234.) Exemplary calcium and zinc chelators include moieties known in the art for chelation of divalent cations, including ethylenediaminetetraacetic acid (EDTA), ethylene glycol bis(beta-aminoethyl ether)-N,N,N',N'-tetraacetic acid, and the like, in addition to those mentioned supra. Exemplary iron chelators include enterobactin, pyridoxal isonicotinyl hydrazones, N,N'-bis(2-hydroxybenzoyl)-ethylenediamine-N,N'-diacetic acid (HBED), and 1-substituted-2-alkyl-3-hydroxy-4-pyridones, including 1-(2'-carboxyethyl)-2-methyl-3-hydroxy-4-pyridone, and other moieties known in the art to chelate iron. Compounds which inhibit NO synthase activity are known in the art and include, e.g., Nγ-substituted arginine analogs, especially of the L-configuration, including L-Nγ-nitro-arginine (a specific inhibitor of cerebral NO synthase), L-Nγ-amino-arginine, and L-Nγ-alkyl-arginines; or an ester thereof, preferably the methyl ester. Exemplary antioxidants include ascorbic acid, tocopherols including alpha-tocopherol, and the like.

In another embodiment, the invention provides a method for inhibiting a convulsive disorder. The method includes the step of administering to a subject in need thereof an effective amount of a dioxapiperazine (also known as diketopiperazine) compound represented by the formula (Formula IV):

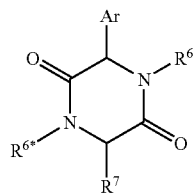

(IV)

where Ar represents an unsubstituted or substituted aryl group; $R^7$ is hydrogen, alkyl, mercaptoalkyl, alkenyl, alkynyl, cycloalkyl, aryl, alkylcarbonyl, arylcarbonyl, alkoxycarbonyl, aryloxycarbonyl, cyano, carboxyl, alkoxycarbonyl, aryloxycarbonyl, or —$(CH_2)_n$—Y, where n is an integer from 1 to 4 and Y is a heterocyclic moiety selected from the group consisting of thiazolyl, triazolyl, and imidazolyl; and $R^6$ and $R^{6*}$ are each independently hydrogen, alkyl, alkylcarbonyl or arylcarbonyl; or a pharmaceutically acceptable salt thereof; such that the convulsive disorder is inhibited. In a preferred embodiment, $R^7$ is not hydrogen, methyl or phenyl. In a preferred embodiment, the compound is cyclo-D-phenylglycyl-(S-Me)-L-cysteine. For synthesis of dioxapiperazines, See, e.g., Kopple, K. D. et al., *J. Org. Chem.* 33:862 (1968); Slater, G. P. *Chem Ind.* (London) 32:1092 (1969); Grahl-Nielsen, O. *Tetrahedron Lett.* 1969:2827 (1969). Synthesis of selected dioxapiperazine compounds is described in the Examples, infra.

In another embodiment, the invention provides a method for concurrently inhibiting epileptogenesis and ictogenesis, the method including the step of administering to a subject in need thereof an effective amount of a compound of the formula:

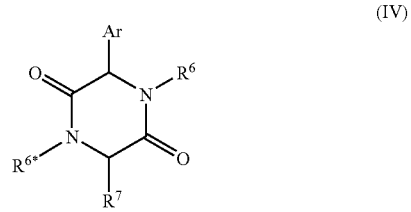

(IV)

where Ar represents an unsubstituted or substituted aryl group; $R^7$ is hydrogen, alkyl, mercaptoalkyl, alkenyl, alkynyl, cycloalkyl, aryl, alkylcarbonyl, arylcarbonyl, alkoxycarbonyl, aryloxycarbonyl, cyano, carboxyl, alkoxycarbonyl, aryloxycarbonyl, or —$(CH_2)_n$—Y, where n is an integer from 1 to 4 and Y is a heterocyclic moiety selected from the group consisting of thiazolyl, triazolyl, and imidazolyl; $R^6$ is hydrogen or alkyl, alkylcarbonyl, arylcarbonyl, alkoxycarbonyl or aryloxycarbonyl; and $R^{6*}$ is selected from the group consisting of an antioxidant moiety, an NMDA antagonist, an NO synthase inhibitor, an iron chelator moiety, a Ca(II) chelator moiety, a Zn(II) chelator moiety, and an antioxidant moiety; or a pharmaceutically acceptable salt thereof; such that epileptogenesis is inhibited. In certain embodiments, $R^7$ is not hydrogen, methyl or phenyl.

In another embodiment, the invention provides a method for treating a disorder associated with NMDA receptor antagonism. The method includes the step of administering to a subject in need thereof an effective amount of a compound of the formula:

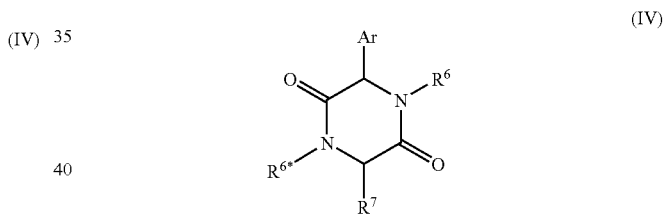

(IV)

where Ar represents an unsubstituted or substituted aryl group; $R^7$ is hydrogen, alkyl, mercaptoalkyl, alkenyl, alkynyl, cycloalkyl, aryl, alkylcarbonyl, arylcarbonyl, alkoxycarbonyl, aryloxycarbonyl, cyano, carboxyl, alkoxycarbonyl, aryloxycarbonyl, or —$(CH_2)_n$—Y, where n is an integer from 1 to 4 and Y is a heterocyclic moiety selected from the group consisting of thiazolyl, triazolyl, and imidazolyl; $R^6$ is hydrogen or alkyl, alkylcarbonyl, arylcarbonyl, alkoxycarbonyl or aryloxycarbonyl; and $R^{6*}$ is an NMDA antagonist moiety; or a pharmaceutically acceptable salt thereof; such that the disorder associated with NMDA receptor antagonism is treated. In certain embodiments, $R^7$ is not hydrogen, methyl or phenyl.

In yet another embodiment, the invention provides a method for inhibiting ictogenesis and epileptogenesis in a subject. The method includes the step of administering to a subject in need thereof an effective amount of an agent represented by the formula A-B, where A is a domain having sodium ion channel blocking activity; and B is a domain having at least one activity selected from the group consisting of NMDA receptor antagonism; GABA inhibition augmentation; calcium binding; iron binding; zinc binding; NO synthase inhibition; and antioxidant activity; such that epileptogenesis is inhibited in the subject. In certain preferred embodiments, the domains A and B (e.g., pharmacophores) of the agent are covalently linked. In certain preferred embodiments, A is a dioxapiperazine moiety, a phenytoin moiety, or a carbamazepine moiety.

In another embodiment, the invention provides a method for inhibiting ictogenesis and epileptogenesis in a subject. The method includes the step of administering to a subject in need thereof an effective amount of an agent represented by the formula A-B, where A is a domain having anti-ictogenic activity; and B is a domain having at least one activity selected from the group consisting of NMDA receptor antagonism; GABA inhibition augmentation; calcium binding; iron binding; zinc binding; NO synthase inhibition; and antioxidant activity; such that epileptogenesis is inhibited in the subject. In certain preferred embodiments, the domains A and B (e.g., pharmacophores) of the agent are covalently linked. In certain preferred embodiments, A is a dioxapiperazine moiety, a phenytoin moiety, or a carbamazepine moiety.

A hybrid drug according to the invention can be a bifunctional molecule created by connecting an anti-ictogenic moiety with an anti-epileptogenic moiety via, preferably, a covalent linkage such as an amide bond or an ester bond. The linkage can optionally be cleavable in vivo. The linkage can also include a linker or spacer moiety to provide flexibility or sufficient space between the A and B moieties to permit interaction with the respective moieties to which A and B bind or with which A and B interact. Exemplary linkers include diacids such as adipic acid, e.g., to link amino group-containing A and B moieties; or diamines such as 1,6-hexanediamine, e.g., to link carboxyl group-containing A and B moieties; or amino acids, e.g., to link an amino-functionalized B moiety to a carboxy-functionalized A moiety or vice versa. A linker can be selected to provide desired properties according to considerations well known to one of skill in the art. The bifunctional molecule thus targets both ictogenesis and epileptogenesis. The skilled practitioner will appreciate that a hybrid drug may comprise one or more desired average pharmacophores.

In another embodiment, a method for inhibiting epileptogenesis and/or ictogenesis in a subject involves administering to a subject an effective amount of a compound such that epileptogenesis is inhibited, where the compound is of Formula X $$R^2\!\!\diagdown\!\!N\!\!-\!\!CH_2CH_2\!\!-\!\!G \atop R^1 \qquad (X)$$

where $R^1$ is hydrogen, alkyl, alkenyl, alkynyl, aryl, alkylcarbonyl, arylcarbonyl, alkoxycarbonyl, or aryloxycarbonyl; $R^2$ is alkyl, alkenyl, alkynyl, aryl, alkylcarbonyl, arylcarbonyl, alkoxycarbonyl, or aryloxycarbonyl; G is an anionic group at physiological pH; and pharmaceutically acceptable salts or esters thereof.

In a preferred embodiment of Formula X, G is carboxyl. In another preferred embodiment of Formula X, $R^1$ is hydrogen. In yet another preferred embodiment of Formula X, $R^2$ is alkyl, e.g., arylalkyl such as phenylalkyl.

Examples of compounds of Formula X include

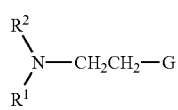

(1)

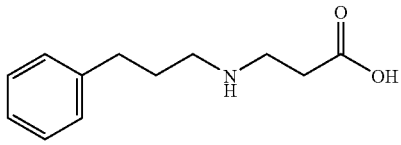

(2)

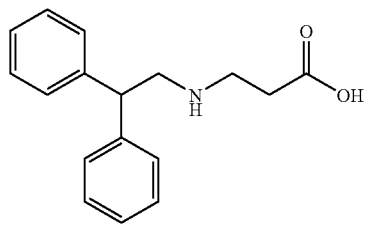

(9)

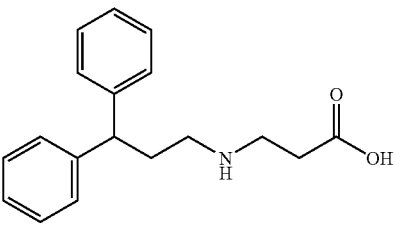

(10)

and pharmaceutically acceptable salts or esters thereof.

In another embodiment, a method for inhibiting epileptogenesis and/or ictogenesis in a subject involves administering to a subject an effective amount of a compound such that epileptogenesis is inhibited, where the compound is either of the following:

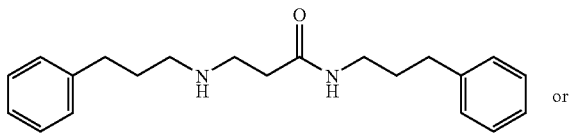

(4)

or

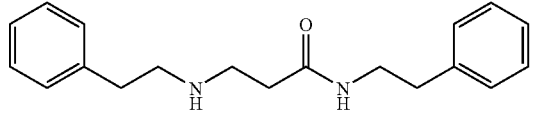

(3)

and pharmaceutically acceptable salts thereof.

In another embodiment, a method for inhibiting epileptogenesis and/or ictogenesis in a subject involves administering to a subject an effective amount of a compound such that epileptogenesis is inhibited, where the compound is of Formula XI

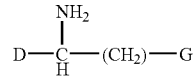

(XI)

wherein G is an anionic group at physiological pH; D is a phenoxy substituted phenyl group; and pharmaceutically acceptable salts or esters thereof.

In a preferred embodiment of Formula XI, G is a carboxyl group. In preferred embodiments of Formula XI, D is an alkylphenoxy substituted phenyl group, e.g., a methylphenoxy substituted phenyl group, or a halophenoxy substituted phenyl group, e.g., a chlorophenoxy substituted phenyl group.

Examples of compounds of Formula XI include

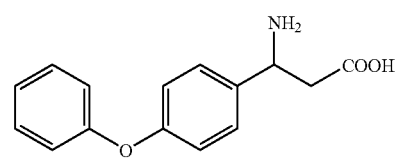
(A13)

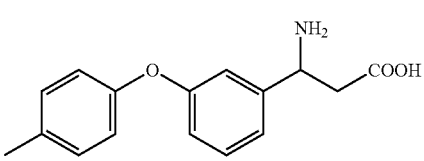
(A14)

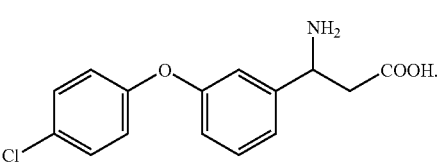
(A16)

and pharmaceutically acceptable salts or esters thereof.

In another embodiment, a method for inhibiting epileptogenesis and/or ictogenesis in a subject involves administering to a subject an effective amount of a compound such that epileptogenesis is inhibited, where the compound is of Formula XII

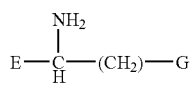
(XII)

where G is an anionic group at physiological pH; E is an aryl group substituted with 2 or more alkoxy or aryloxy moieties; and pharmaceutically acceptable salts or esters thereof In a preferred embodiment of Formula XII, G is a carboxyl group. In another preferred embodiment of Formula XII, E is a phenyl group substituted with 2 or more alkoxy or aryloxy moieties. In another preferred embodiment of Formula XII, E is a phenyl group substituted with 2 or more alkoxy (i.e. methoxy) groups.

Examples of compounds of Formula XII include

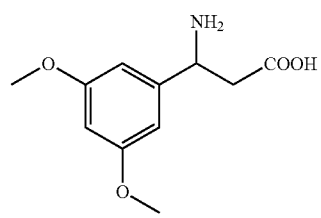
(A29)

-continued

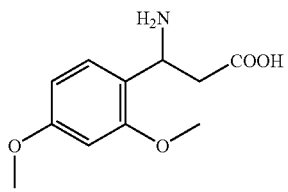
(A30)

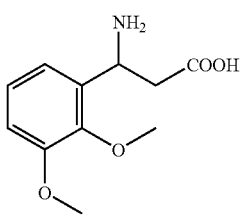
(A31)

and pharmaceutically acceptable salts thereof.

In another embodiment, a method for inhibiting epileptogenesis and/or ictogenesis in a subject, comprises administering to a subject an effective amount of a compound such that epileptogenesis is inhibited, where the compound is of Formula XIII

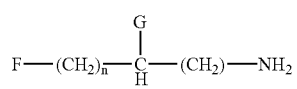
(XIII)

where G is an anionic group at physiological pH; n is 1 to 3; F is a phenyl substituted methyl; and pharmaceutically acceptable salts or esters thereof.

In a preferred embodiment of Formula XIII, G is a carboxyl group. In another preferred embodiment of Formula XIII, n is 1 and F is a diphenyl substituted methyl.

Examples of compounds of Formula XIII include

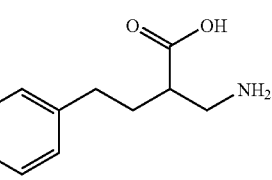
(7)

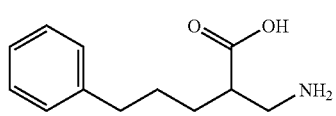
(8)

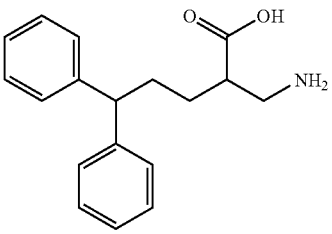
(14)

-continued

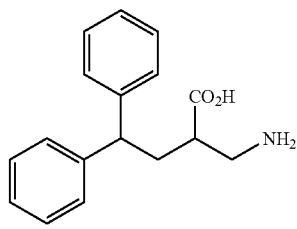
(13)

and pharmaceutically acceptable salts or esters thereof.

Compounds which find use in the therapeutic methods of the invention can be determined through routine screening assays. For example, the animal model of Phase 1 epileptogenesis described in the Examples, infra, can be employed to determine whether a particular compound has anti-epileptogenic activity against Phase 1 epileptogenesis. Chronic epileptogenesis can be modeled in rats (and candidate compounds screened with) the kindling assay described by Silver et al. (*Ann. Neurol.* (1991) 29:356). Similarly, compounds useful as anticonvulsants can be screened in conventional animal models, such as the mouse model described in Horton, R. W. et al., *Eur. J. Pharmacol.* (1979) 59:75-83. Compounds or pharmacophores useful for, e.g., binding to or inhibition of receptors or enzymes can be screened according to conventional methods known to the ordinarily skilled practitioner. For example, binding to the GABA uptake receptor can be quantified by the method of Ramsey et al. as modified by Schlewer (Schlewer, J., et al., *J. Med. Chem.* (1991) 34:2547). Binding to the glycine site on an NMDA receptor can be quantified, e.g., according to the method described in Kemp, A., et al., *Proc. Natl. Acad. Sci. USA* (1988) 85:6547. Effect on the voltage-gated $Na^+$ channel can be evaluated in vitro by voltage clamp assay in rat hippocampal slices.

Assays suitable for screening candidate compounds for anticonvulsive and/or anti-epileptogenic activity in mice or rats are described in the Examples, infra.

III. Compounds for Use in the Methods of the Invention

In another aspect, the invention provides compounds useful for the treatment of epilepsy and convulsive disorders, including epileptogenesis and ictogenesis.

In one embodiment, the invention provides a dioxapiperazine compound of the formula (Formula IV)

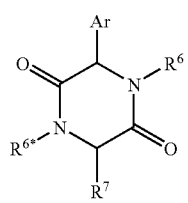
(IV)

where Ar represents an unsubstituted or substituted aryl group; $R^7$ is hydrogen, alkyl, mercaptoalkyl, alkenyl, alkynyl, cycloalkyl, aryl, alkylcarbonyl, arylcarbonyl, alkoxycarbonyl, aryloxycarbonyl, cyano, carboxyl, alkoxycarbonyl, aryloxycarbonyl, or —$(CH_2)_n$—Y, where n is an integer from 1 to 4 and Y is hydrogen or a heterocyclic moiety selected from the group consisting of thiazolyl, triazolyl, and imidazolyl; and $R^6$ and $R^{6*}$ are each independently hydrogen, alkyl, alkylcarbonyl, arylcarbonyl, alkoxycarbonyl or aryloxycarbonyl; or a pharmaceutically acceptable salt thereof. In some preferred embodiments, the carbon atom to which the Ar group is attached has the D configuration. In certain embodiments, Ar is an unsubstituted or substituted phenyl group. In certain embodiments, Y is hydrogen. In certain preferred embodiments, at least one of $R^6$ and $R^{6*}$ is selected from the group consisting of an antioxidant moiety, an NMDA antagonist, an NO synthase inhibitor, an iron chelator moiety, a Ca(II) chelator moiety, and a Zn(II) chelator moiety. In certain preferred embodiments, $R^7$ is methyl or mercaptomethyl. In certain preferred embodiments, $R^6$ and $R^{6*}$ are both hydrogen. In certain particularly preferred embodiments, the compound is cyclophenylglycyl-2-(amino-3-mercaptobutanoic acid), more preferably cyclo-D-phenylglycyl-L-{2-(amino-3-mercaptobutanoic acid)}. In a preferred embodiment, the compound is cyclo-D-phenylglycyl-(S-Me)-L-cysteine. In some preferred embodiments, Ar is an unsubstituted phenyl group. In certain embodiments, $R^7$ is not hydrogen, methyl or phenyl.

In another embodiment, the invention provides a compound of the formula (Formula IV)

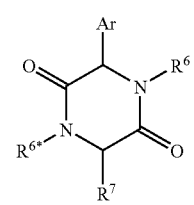
(IV)

where Ar represents an unsubstituted or substituted aryl group; $R^7$ is, alkyl, mercaptoalkyl, alkenyl, alkynyl, cycloalkyl, aryl, alkylcarbonyl, arylcarbonyl, alkoxycarbonyl, aryloxycarbonyl, cyano, carboxyl, alkoxycarbonyl, aryloxycarbonyl, or —$(CH_2)_n$—Y, where n is an integer from 1 to 4 and Y is hydrogen or a heterocyclic moiety selected from the group consisting of thiazolyl, triazolyl, and imidazolyl; $R^6$ is hydrogen or alkyl, alkylcarbonyl, arylcarbonyl, alkoxycarbonyl or aryloxycarbonyl; and $R^{6*}$ is selected from the group consisting of an antioxidant moiety, an NMDA antagonist, an NO synthase inhibitor, an iron chelator moiety, a Ca(II) chelator moiety, and a Zn(II) chelator moiety; or both $R^6$ and $R^{6*}$ are selected from the group consisting of an antioxidant moiety, an NMDA antagonist, an NO synthase inhibitor, an iron chelator moiety, a Ca(II) chelator moiety, and a Zn(II) chelator moiety; or a pharmaceutically acceptable salt thereof. In certain preferred embodiments, $R^{6*}$ is D-α-aminoadipyl. In certain preferred embodiments, $R^7$ is mercaptomethyl. In certain embodiments, $R^7$ is not hydrogen, methyl or phenyl. In certain preferred embodiments, $R^{6*}$ further comprises a cleavable linkage. In one embodiment, the compound comprises cyclo-D-phenylglycyl-L-alanine.

The compounds of the invention include compounds which can have a single pharmacophore (e.g., dioxapiperazines where the dioxapiperazine moiety is the sole pharmacophore); or β-amino anionic moieties where the β-amino anionic moiety is responsible for the biochemical activity of the compound. Certain compounds of the invention include two distinct pharmacophores and have a structure represented by A-B, where A and B are each domains or pharmacophores having biochemical activity (e.g., an anticonvulsant dioxapiperazine moiety having a distinct antioxidant moiety, e.g., $R^{6*}$) (also referred to herein as a "hybrid" drug). A compound which includes two pharmacophores can be capable of interaction with two or more distinct receptors. Where the compound of the invention includes more than one pharmacophore, the pharmacophores can be linked to each other by a variety of techniques known to the skilled practitioner. For example, the pharmacophore represented by $R^{6*}$ can be covalently bonded to a dioxapiperazine moiety through an amide linkage to a nitrogen of the dioxapiperazine ring. A linkage between two pharmacophores can be selected such that the two pharmacophores are cleaved from each other in vivo (e.g., by the selection of a linkage which is labile in vivo). Examples of such biologically labile linkages are known in the art. See, e.g., Silverman, cited above. Advantageously, such a "hybrid" two-pharmacophore drug can be designed to be transported within the body to reach a site or organ such as the brain, where one or more pharmacophore moieties exert a biological effect, at which site the hybrid drug can be cleaved to provide two active drug moieties. Some examples of hybrid drugs are set forth above.

The invention further contemplates the use of prodrugs which are converted in vivo to the therapeutic compounds of the invention. Such prodrugs can be used to alter the biodistribution (e.g., to allow compounds which would not typically cross the blood-brain barrier to cross the blood-brain barrier) or the pharmacokinetics of the therapeutic compound. For example, an anionic group, e.g., a carboxylate or sulfonate, can be esterified, e.g., with a methyl group or a phenyl group, to yield a carboxylate or sulfonate ester. When the carboxylate or sulfonate ester is administered to a subject, the ester is cleaved, enzymatically or non-enzymatically, to reveal the anionic group. Such an ester can be cyclic, e.g., a lactone or sultone, or two or more anionic moieties may be esterified through a linking group. An anionic group can be esterified with moieties (e.g., acyloxymethyl esters) which are cleaved to reveal an intermediate compound which subsequently decomposes to yield the active compound. Alternatively, an anionic moiety can be esterified to a group which is actively transported in vivo, or which is selectively taken up by target organs. The ester can be selected to allow specific targeting of the therapeutic moieties to particular organs. In another embodiment, the prodrug is a reduced form of an anionic group, e.g., a carboxylate or sulfonate, e.g., an alcohol or thiol, which is oxidized in vivo to the therapeutic compound.

Thus, as described above, preferred compounds include pyrimidines, such as substituted uracils, which can be converted in vivo to β-amino anionic compounds. In a preferred embodiment, the compound can be represented by the formula (Formula V):

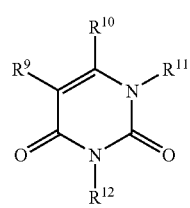

(V)

where $R^9$ and $R^{10}$ are each independently selected from the group consisting of hydrogen, alkyl (including cycloalkyl, heterocyclyl, and aralkyl), alkenyl, alkynyl, aryl, alkoxy, aryloxy, alkylcarbonyl, arylcarbonyl, alkoxycarbonyl, aryloxycarbonyl, amino (including unsubstituted and substituted amino), hydroxy, thiol, alkylthiol, nitro, cyano, halogen, carboxyl, alkoxycarbonyloxy, aryloxycarbonyloxy or aminocarbonyl; or $R^9$ and $R^{10}$, together with the two-carbon unit to which they are attached, are joined to form a carbocyclic or heterocyclic ring having from 4 to 8 members in the ring; and $R^{11}$ is hydrogen, alkyl, alkenyl, alkynyl, cycloalkyl, aryl, alkylcarbonyl, arylcarbonyl, alkoxycarbonyl, or aryloxycarbonyl; or $R^{10}$ and $R^{11}$, together with the carbon atom and nitrogen atom to which they are respectively attached, are joined to form a heterocyclic ring having from 4 to 8 members in the ring; and $R^{12}$ is selected from the group consisting of hydrogen, alkyl, aryl and a carbohydrate (such as a sugar like ribose or deoxyribose); or a pharmaceutically acceptable salt or ester thereof. In another embodiment, the compound can be represented by the formula (Formula Va):

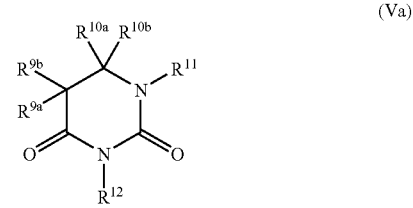

(Va)

where $R^{9a}, R^{9b}, R^{10a}, R^{10b}$ are each independently selected from the group consisting of hydrogen, alkyl (including cycloalkyl, heterocyclyl, and aralkyl), alkenyl, alkynyl, aryl, alkoxy, aryloxy, alkylcarbonyl, arylcarbonyl, alkoxycarbonyl, aryloxycarbonyl, amino (including unsubstituted and substituted amino), hydroxy, thiol, alkylthiol, nitro, cyano, halogen, carboxyl, alkoxycarbonyloxy, aryloxycarbonyloxy or aminocarbonyl; or $R^{9a}$ and $R^{9b}$, together with the two-carbon unit to which they are attached, are joined to form a carbocyclic or heterocyclic ring having from 4 to 8 members in the ring; or $R^{10a}$ and $R^{10b}$, together with the two-carbon unit to which they are attached, are joined to form a carbocyclic or heterocyclic ring having from 4 to 8 members in the ring; or one of $R^{9a}$ and $R^{9b}$ is joined with one of $R^{10a}$ and $R^{10b}$, together with the two-carbon unit to which they are attached, to form a carbocyclic or heterocyclic ring having from 4 to 8 members in the ring; $R^{11}$ is hydrogen, alkyl, alkenyl, alkynyl, cycloalkyl, aryl, alkylcarbonyl, arylcarbonyl, alkoxycarbonyl, or aryloxycarbonyl; or one of $R^{10b}$ and $R^{10b}$ is joined with $R^{11}$, together with the carbon atom and nitrogen atom to which they are respectively attached, to form a heterocyclic ring having from 4 to 8 members in the ring; and $R^{12}$ is selected from the group consisting of hydrogen, alkyl, aryl and a carbohydrate (such as a sugar, e.g., ribose or deoxyribose); or a pharmaceutically acceptable salt or ester thereof.

A preferred group of compounds according to the invention include

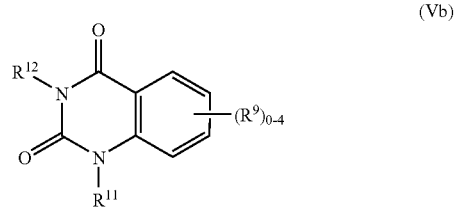

(Vb)

where $R^9$ (each selected independently of other $R^9$ groups, if any), $R^{11}$, and $R^{12}$ are defined above.

Another preferred group of compounds include

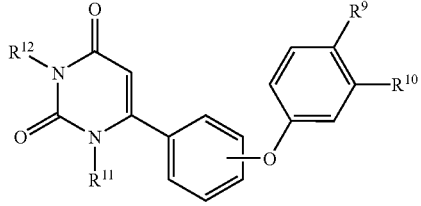
(Vc)

where $R^9$, $R^{10}$, $R^{11}$, and $R^{12}$ are defined above. More preferred are the following compounds

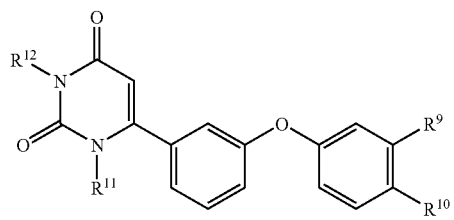
(meta-Vc)

where $R^9$, $R^{10}$, $R^{11}$, and $R^{12}$ are defined above.

Still another preferred group of compounds include

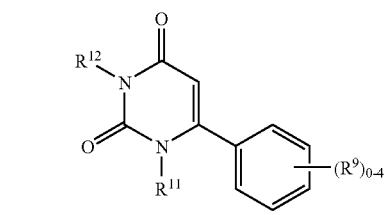
(Vd)

where $R^9$ (each selected independently of other $R^9$ groups, if any), $R^{11}$, and $R^{12}$ are defined above.

Also within the scope of the invention are the corresponding dihydrouracil compounds:

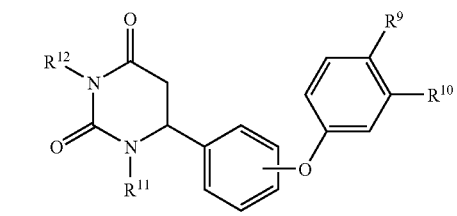
(Ve)

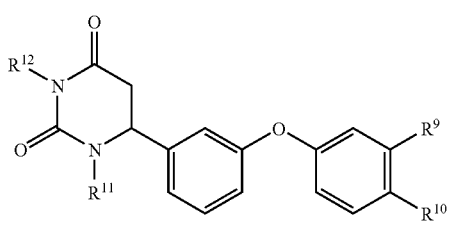
(meta-Ve)

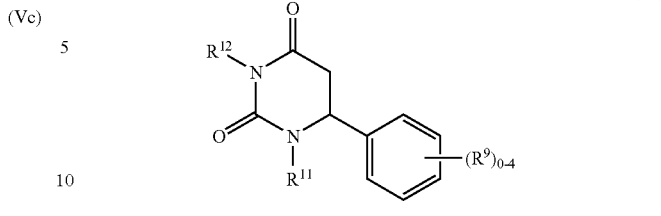
(Vf)

where $R^9$ (each selected independently of other $R^9$ groups, if any), $R^{10}$, $R^{11}$, and $R^{12}$ are defined above, and including all possible stereoisomers.

Figure 2:
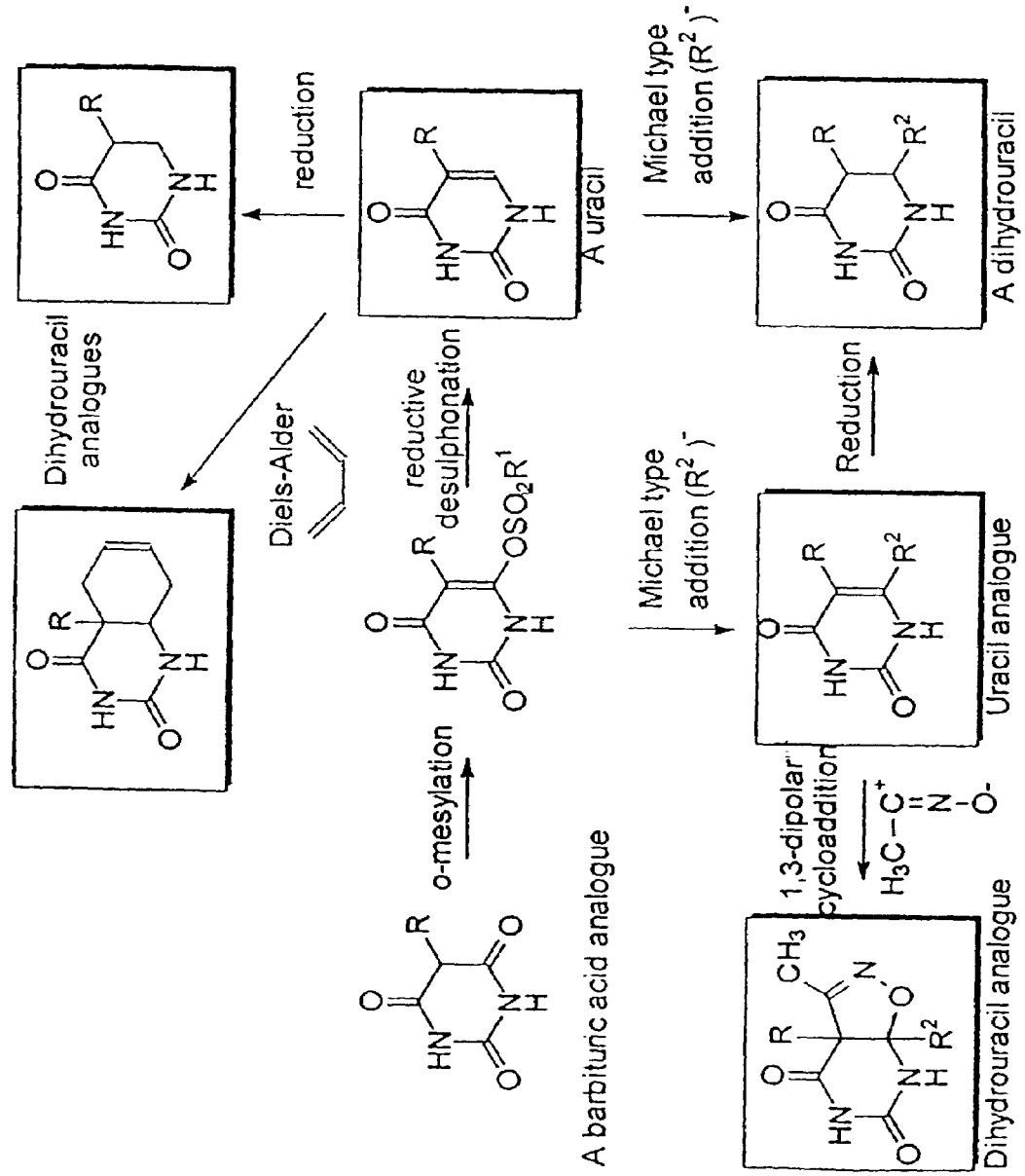
FIG. 2 depicts exemplary synthetic schemes for preparing pyrimidine and dihydropyrimidine compounds of the invention.

Compounds of Formulas V-Vf can be prepared according to a variety of synthetic procedures, some of which are known in the art. Exemplary syntheses are shown in FIG. 2. For example, as shown in FIG. 2, a barbituric acid compound can be modified (e.g., by mesylation with mesyl chloride and an amine base) to provide a compound which can be further functionalized (e.g., by Michael addition of a suitable nucleophile); or can be reductively desulphonated to provide a dienophile for subsequent Diels-Alder cycloaddition with a suitable dienophile. Reduction of the uracil ring provides dihydrouracil derivatives.

Compounds useful in the present invention may also include carrier or targeting moieties which allow the therapeutic compound to be selectively delivered to a target organ or organs. For example, if delivery of a therapeutic compound to the brain is desired, the compound may include a moiety capable of targeting the compound to the brain, by either active or passive transport (a "targeting moiety"). Illustratively, the carrier molecule may include a redox moiety, as described in, for example, U.S. Pat. Nos. 4,540,564 and 5,389,623. These patents disclose drugs linked to dihydropyridine moieties which can enter the brain, where they are oxidized to a charged pyridinium species which is trapped in the brain. Thus, drug accumulates in the brain. Other carrier moieties include compounds, such as amino acids or thyroxine, which can be passively or actively transported in vivo. Such a carrier moiety can be metabolically removed in vivo, or can remain intact as part of an active compound. Many targeting moieties are known, and include, for example, asialoglycoproteins (see, e.g., U.S. Pat. No. 5,166,320) and other ligands which are transported into cells via receptor-mediated endocytosis.

The targeting and prodrug strategies described above can be combined to produce a compound that can be transported as a prodrug to a desired site of action and then unmasked to reveal an active compound.

The invention further provides a kit which includes a container of a compound of the invention and instructions for administering a therapeutically effective amount of the compound to a subject in need thereof such that a convulsive disorder (e.g., epileptogenesis) is inhibited in the subject. The kits of the invention provide convenient means for administering the compounds of the invention. In a particularly preferred embodiment, the kit includes a therapeutically effective amount of the compound, more preferably in unit dosage form.

IV. Libraries

In another aspect, the invention provides libraries of compounds of Formula IV, Formula V-Vf, or Formula XIV, and methods of preparing such libraries.

The synthesis of combinatorial libraries is well known in the art and has been reviewed (see, e.g., E. M. Gordon et al., *J. Med. Chem.* 37:1385-1401 (1994)). Thus, the invention includes methods for synthesis of combinatorial libraries of compounds of Formula IV, Formula V-Vf, or Formula XIV. Such libraries can be synthesized according to a variety of methods. For example, a "split-pool" strategy can be implemented to produce a library of compounds. The library of immobilized compounds can then be washed to remove impurities. In certain embodiments, the immobilized compounds can be cleaved from the solid support to yield a compound of Formula IV, Formula V-Vf, or Formula XIV.

In another illustrative method of combinatorial synthesis, a "diversomer library" is created by the method of Hobbs, DeWitt et al. (*Proc. Natl. Acad. Sci. U.S.A.* 90:6909 (1993)). After creation of the library of compounds, purification and workup yields a soluble library of substituted compounds of Formula IV, Formula V-Vf, or Formula XIV.

Other synthesis methods, including the "tea-bag" technique of Houghten et al., *Nature* 354:84-86 (1991), can also be used to synthesize libraries of compounds according to the subject invention.

Combinatorial libraries can be screened to determine whether any members of the library have a desired activity, and, if so, to identify the active species. Methods of screening combinatorial libraries have been described (see, e.g., Gordon et al., *J Med. Chem.*, op. cit.). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, calorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening the libraries of the invention are known in the art (see, e.g., E. M. Gordon et al., *J. Med. Chem.* 37:1385-1401 (1994)).

Combinatorial libraries of compounds can also be synthesized with "tags" to encode the identity of each member of the library. See, e.g., U.S. Pat. No. 5,565,324 and PCT Publication No. WO 94/08051). In general, this method features the use of inert, but readily detectable, tags, that are attached to the solid support or to the compounds. When an active compound is detected such as by one of the techniques described above, the identity of the compound is determined by identification of the unique accompanying tag. This tagging method permits the synthesis of large libraries of compounds which can be identified at very low levels.

In preferred embodiments, the libraries of compounds of the invention contain at least 30 compounds, more preferably at least 100 compounds, and still more preferably at least 500 compounds. In preferred embodiments, the libraries of compounds of the invention contain fewer than $10^9$ compounds, more preferably fewer than $10^8$ compounds, and still more preferably fewer than $10^7$ compounds.

A library of compounds is preferably substantially pure, i.e., substantially free of compounds other than the intended products, e.g., members of the library. In preferred embodiments, the purity of a library produced according to the methods of the invention is at least about 50%, more preferably at least about 70%, still more preferably at least about 90%, and most preferably at least about 95%.

The libraries of the invention can be prepared as described herein. In general, at least one starting material used for synthesis of the libraries of the invention is provided as a variegated population. The term "variegated population", as used herein, refers to a population including at least two different chemical entities, e.g., of different chemical structure. For example, a "variegated population" of compounds of Formula XIV would comprise at least two different compounds of Formula XIV. Use of a variegated population of linkers to immobilize compounds to the solid support can produce a variety of compounds upon cleavage of the linkers.

Libraries of the invention are useful for, inter alia, drug discovery. For example, a library of the invention can be screened to determine whether the library includes compounds having a pre-selected activity, e.g., anti-epileptogenic or anticonvulsant activity.

V. Pyrimidine and Uracil Compounds and Uses Thereof in the Methods of the Invention This invention provides anti-ictogenic and/or anti-epileptogenic compounds of the formula (Formula XIV)

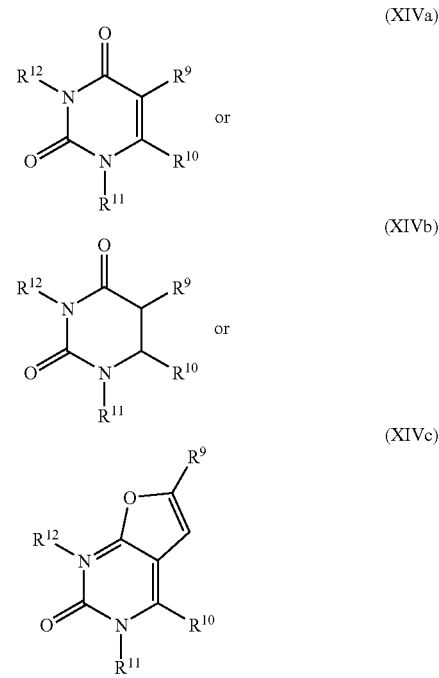

(i.e., Formulas XIVa, XIVb, and XIVc, respectively) where $R^9$ is hydrogen, alkyl, alkynyl, aryl, amino, hydroxy, halogen, nitro, carboxyl, or $R^9$ and $R^{10}$ together form a 5- or 6-membered carbocyclic or heterocyclic ring; $R^{10}$ is hydrogen, alkyl, aryl, carboxyl, or $R^9$ and $R^{10}$ together form a 5- or 6-membered carbocyclic or heterocyclic ring; $R^{11}$ is hydrogen, alkyl, aryl (including hydroxyalkyl), thioether, amino, or tetrahydrofuranyl (including substituted tetrahydrofurans, such as ribose and other carbohydrates); and $R^{12}$ is hydrogen, alkyl (including hydroxyalkyl), aryl, amino, or thioether; or pharmaceutically acceptable salts or esters thereof.

In an embodiment, $R^9$ is alkyl such as methyl, ethyl, propyl, and butyl or hydroxyalkyl (i.e. hydroxymethyl, hydroxyethyl, hydroxypropyl, and hydroxybutyl). Desirably $R^9$ is bromine, fluorine, chlorine, or iodine. More desirably, $R^9$ is alkynyl (i.e. ethynyl, propynyl, butynyl, pentynyl, and hexynyl). Desirably, $R^9$ is thioether.

In an embodiment, $R^{10}$ is hydrogen. Desirably $R^{10}$ is alkyl (e.g. methyl, ethyl, propyl, or butyl.) In an embodiment of the above compounds, $R^{11}$ is hydrogen, or alternately alkyl such as isopropyl, sec-butyl, arylalkyl, or phenylalkyl (e.g., nitro-substituted phenylalkyl.) In another embodiment, $R^{12}$ is hydrogen, or alternately alkyl, such as arylalkyl or phenylalkyl (e.g., nitro-substituted phenylalkyl).

In an example of the above compounds, $R^9$ is bromine, $R^{10}$ is hydrogen, and $R^{12}$ is hydrogen. In another example, $R^{10}$ is hydrogen, $R^{11}$ is arylalkyl, and $R^{12}$ is hydrogen.

Some preferred $R^{11}$ and $R^{12}$ groups include hydrogen, methyl, ethyl, isopropyl, sec-butyl, benzyl (including para-nitrobenzyl), and cyclohexylmethyl.

In another embodiment of the above compounds, $R^9$ is hydrogen, $R^{10}$ is hydrogen, $R^{11}$ is arylalkyl, and $R^{12}$ is hydrogen. In still another embodiment of the above compounds, $R^9$ is bromine, $R^{10}$ is hydrogen, $R^{11}$ is arylalkyl, and $R^{12}$ is hydrogen.

Examples of the above compounds include compounds P1-P43 (see Table, below) and pharmaceutically acceptable salts and esters thereof.

Any of the above compounds may be formulated in combination with a pharmaceutically acceptable carrier. For example, an anti-convulsive pharmaceutical composition can include an amount of one or more of the above compounds effective to inhibit a convulsive disorder such as epilepsy in a subject in need thereof, and a pharmaceutically acceptable carrier. Ictogenesis may be treated or prevented in a subject in need thereof by administering to the subject an amount of one or more of the above compounds to inhibit ictogenesis in the subject so that ictogenesis is treated or prevented in the subject. In another aspect, epileptogenesis may be treated or prevented in a subject in need thereof by administering to the subject an amount of one or more of the above compounds to inhibit epileptogenesis in the subject so that epileptogenesis is treated or prevented in the subject.

In addition, kits for treating or preventing ictogenesis (or epileptogenesis) in a subject may include one of the above compounds, and instructions for administering a therapeutically effective amount of a compound to the subject so that ictogenesis (or epileptogenesis) is treated or prevented in the subject.

This invention further encompasses a method of diagnosing an epileptogenic condition in a subject including administering one of the above compounds labeled with a detectable marker to the subject; and measuring increased binding of the compound to the NMDA receptors of the neurons of the subject's brain so that an epileptogenic condition is diagnosed in the subject.

"Compound labeled with a detectable marker" as used herein includes compounds that are labeled by a detectable means and includes enzymatically, radioactively, fluorescently, chemiluminescently, and/or bioluminescently labeled antibodies.

Examples of enzymes that can be used as labeled include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

Examples of radioactive labels include $^3H$, $^{125}I$, $^{131}I$, $^{35}S$, and $^{14}C$, where $^{125}I$ is preferred. Examples of fluorescent labels include fluorescein isothiocyanate, rhodamine, phycoerytherin, phycocyanin, allophycocyanin, o-phthaldehyde and fluorescamine. Examples of chemiluminescent labels include luminol, luciferin, isoluminol, theromatic acridinium ester, imidazole, acridinium salt and oxalate ester. Examples of bioluminescent labels include luciferin, luciferase and aequorin.

This invention further relates to a method of treating or preventing seizures, e.g., epileptic seizures, in a subject suffering from head trauma including administering to the subject an amount of one of the above compounds so that seizures are treated or prevented in the subject.

Although compounds according to Formulas Vb-Vf and XIV are preferred in the present invention, compounds according to Formulas V-Vf, IV, X, XI, XII, and XIII, as well as those disclosed in PCT publication WO 98/40055 and corresponding U.S. and other national and regional phase applications and patents, may also be used in the methods of the present invention.

VI. Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. The pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. In a preferred embodiment, the therapeutic compound is administered orally. The compounds of the invention can be formulated as pharmaceutical compositions for administration to a subject, e.g., a mammal, including a human.

The compounds of the invention are administered to subjects in a biologically compatible form suitable for pharmaceutical administration in-vivo. By "biologically compatible form suitable for administration in vivo" is meant a compound to be administered where any toxic effects are outweighed by the therapeutic effects of the compound. The term subject is intended to include living organisms where an immune response can be elicited, e.g., mammals. Examples of subjects include humans, dogs, cats, mice, rats, and transgenic species thereof. Administration of a therapeutically active amount of the therapeutic compositions of the present invention is defined as an amount effective, at dosages and for periods of time necessary to achieve the desired result. For example, a therapeutically active amount of a compound of the invention may vary according to factors such as the disease state, age, sex, and weight of the individual, and the ability of compound to elicit a desired response in the individual. Dosage regimes may be adjusted to provide the optimum therapeutic response. For example, several divided doses may be administered daily or the dose may be proportionally reduced as indicated by the exigencies of the therapeutic situation.

The active compound may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound.

A compound of the invention can be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. To administer a compound of the invention by other than parenteral administration, it may be necessary to coat the compound with, or co-administer the compound with a material to prevent its inactivation. Liposomes include water-in-oil-in-water emulsions as well as conventional liposomes (Strejan et al., (1984) *J. Neuroimmunol* 7:27). The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

When the active compound is suitably protected, as described above, the composition may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the therapeutic treatment of individuals.

EXAMPLES

General Methods

All chemicals used as starting material were purchased from Aldrich Chemical Company (St. Louis, Mo.) and used with no further purification unless otherwise stated in the experimental section. All chemical reactions were carried out under nitrogen or argon atmosphere, except the nitration of 6-methyluracil, which was open to atmospheric air. Thin layer chromatography (TLC) was performed on pre-coated Brinkmann silica gel 60 F254 plates with aluminum backing. Resolved TLCs were visualized with iodine vapor and UV light. Melting points (MP) were obtained using a MelTemp II capillary apparatus, and the values are uncorrected. The proton ($^1$H) and carbon ($^{13}$C) nuclear magnetic resonance (NMR) spectra were recorded at 300 and 75 MHz, respectively, with a Bruker Avance AC-300 spectrometer using DMSO-$d_6$ as the solvent. $^1$H and $^{13}$C chemical shifts are reported as δ values in parts per millions (ppm) relative to tetramethylsilane (TMS). Signals are expressed as s (singlet), d (doublet), t (triplet), m (multiplet) and br (broad). $^1$H NMR coupling constants are reported in Hertz (Hz) and refer to the apparent multiplicities as given on spectra. Molecular masses were obtained from spectra recorded on a VG Quattro Mass spectrometer with electron impact (EI) or chemical ionization (CI). Infrared (IR) spectra were recorded on a Bomem MB-120 spectrometer using KBr disks. The signals are reported in cm$^{-1}$, and expressed as s (strong), m (medium), w (weak), and br (broad).

The following preferred compounds of the invention were synthesized according to the methods described herein: 5-hydroxymethyluracil, 5-tosylmethyluracil, 5-hexynyluracil, 6-n-butylfuranopyrimidin-2-one, 5-bromouracil, 5-bromo-1-benzyluracil, 5-bromo-1-isopropyluracil, 5-bromo-1-p-nitrobenzyluracil, 5-bromo-1,3-bis(p-nitrobenzyl)uracil, 5-bromo-1-cyclohexylmethyluracil, 5-bromo-1,3-dicyclohexylmethyluracil, 5-bromo-1-isobutyluracil 6-methyl-1-benzyluracil, 1-benzyluracil, and 5-bromo-6-methyluracil.

Preferred compounds of the invention also include 1H-pyrimidine-2,4-dione, 5-methyl-1H-pyrimidine-2,4-dione, 5-hydroxymethyl-1H-pyrimidine-2,4-dione, 5-hydroxy-1H-pyrimidine-2,4-dione, 5-bromo-1H-pyrimidine-2,4-dione, 5-iodo-1H-pyrimidine-2,4-dione, 6-methyl-1H-pyrimidine-2,4-dione, 5-bromo-6-methyl-1H-pyrimidine-2,4-dione, 6-methyl-5-nitro-1H-pyrimidine-2,4-dione, 5-amino-2,6-dioxo-1,2,3,6-tetrahydro-pyrimidine-4-carboxylic acid, 2,6-dioxo-1,2,3,6-tetrahydro-pyrimidine-4-carboxylic acid, 2,4-dioxo-1,2,3,4-tetrahydro-pyrimidine-5-carboxylic acid, 1,3-dimethyl-5-nitro-1H-pyrimidine-2,4-dione, 5,6-dimethyl-1H-pyrimidine-2,4-dione, 1H-quinazoline-2,4-dione, 3,9-dihydro-purine-2,6-dione, 6-butyl-3H-furo[2,3-d]pyrimidin-2-one, 5-hex-1-ynyl-1H-pyrimidine-2,4-dione, 1-(4-hydroxy-5-hydroxymethyl-tetrahydro-furan-2-yl)-5-methyl-1H-pyrimidine-2,4-dione, 5-bromo-1-sec-butyl-1H-pyrimidine-2,4-dione, 5-bromo-1-isopropyl-1H-pyrimidine-2,4-dione, 1-benzyl-5-bromo-1H-pyrimidine-2,4-dione, 5-bromo-1-cyclohexylmethyl-1H-pyrimidine-2,4-dione, 5-bromo-1,3-bis-cyclohexylmethyl-1H-pyrimidine-2,4-dione, 5-bromo-1,3-bis-(4-nitro-benzyl)-1H-pyrimidine-2,4-dione, 1-benzyl-1H-pyrimidine-2,4-dione, 1-benzyl-6-methyl-1H-pyrimidine-2,4-dione, 1,3-dibenzyl-5-hex-1-ynyl-1H-pyrimidine-2,4-dione, 1-benzyl-5-hex-1-ynyl-1H-pyrimidine-2,4-dione, and 3-benzyl-6-butyl-3H-furo[2,3-d]pyrimidin-2-one.

Still more preferred compounds include 5-methylsulfanylmethyl-1H-pyrimidine-2,4-dione, 1-benzyl-5-iodo-1H-pyrimidine-2,4-dione, 6-methyl-1,3-bis-(4-nitro-benzyl)-1H-pyrimidine-2,4-dione, 1-methyl-1H-pyrimidine-2,4-dione, 1,3-dimethyl-1H-pyrimidine-2,4-dione, 1,3-diisopropyl-1H-pyrimidine-2,4-dione, 1,3-bis-(3-hydroxy-propyl)-1H-pyrimidine-2,4-dione, 3-amino-1-benzyl-dihydro-pyrimidine-2,4-dione, 3-amino-1-benzyl-6-methyl-dihydro-pyrimidine-2,4-dione, 6-phenyl-dihydro-pyrimidine-2,4-dione, 6-m-tolyl-dihydro-pyrimidine-2,4-dione, and 1-(3-amino-phenyl)-1H-pyrazole-4-carboxylic acid amide.

Synthesis of 5-hydroxymethyluracil

To a 40 mL aqueous solution containing 0.60 gram of KOH were added 1.2 g of uracil and 5 mL of a 36.5% aqueous solution of formaldehyde. The resulting mixture was stirred in an oil bath set at 50° C. and the reaction was allowed to proceed until the complete disappearance of the starting uracil as observed by thin layer chromatography (TLC). The total reaction time was 72 hours under a nitrogen atmosphere. The reaction mixture was diluted with 80 mL of distilled water and vigorously stirred as 2.0 g of Amberlite resin IRC-50 (H) was added. The mixture was stirred for an extra 30-minute period and the pH was verified to ensure that the mixture was slightly acidic before proceeding. The resin was removed by filtration, and the filtrate was concentrated by vacuum distillation to a volume of approximately 25 mL. The solution was allowed to cool to room temperature, then further cooled in an ice bath to precipitate the product as a white solid. Recrystallization of the product was performed from water-methanol (volume ratio 1:2) and the product was filtered out, washed with cold methanol and dried under high vacuum to yield 827 mg of a fine white powder (54.4% yield) showing a single on TLC, with the $R_f$ value 0.69 (methanol solvent) and properties given below.

Observed Properties of 5-hydroxymethyluracil

| | |
|---|---|
| MP (° C.) | >300 (decomposes) |
| Molecular mass | 141.9 (EI) |
| IR (cm$^{-1}$) | 3373 (s), 2850-3100 (s, br), 1650-1700 (s, br), 1531 (s), 1163 (s), 1000 (s), 927 (s), 855 (s), 777 (s), 592 (s), 546 (s) |
| $^1$H NMR (ppm) | 4.12, 7.27 |
| $^{13}$C NMR (ppm) | 55.72, 112.59, 138.17, 151.25, 163.71 |

Synthesis of 1,3-bis-(methylthiomethyl)uracil

A mixture of 5.0 mL of DMSO and 500 mg of uracil was stirred at 150° C. in an oil bath until complete disappearance of the starting uracil (72 hours). The reaction progress was monitored by TLC using silica gel plates and a solvent system made of ethylacetate (EtOAc), methanol (MeOH) and hexanes in the proportions of 10:1:3 by volume. After 72 hours, the reaction mixture was distilled at reduced pressure to remove the excess of DMSO and other volatiles. The resulting yellow oil was dissolved in acetone and the resulting solution was treated with activated charcoal to remove impurities. Then, the charcoal mixture was filtered through celite to obtain a pale yellow solution. The acetone was removed under reduced pressure to yield a viscous clear oil that was dissolved in ethanol; and the product was precipitated out as a white solid by drop-wise addition of water. Excess water was avoided; otherwise, a yellow oil also precipitates from the solution. The product was gathered by filtration, washed with diethyl ether and dried under high vacuum to obtain 328.1 mg (31.7% yield) of a white crystalline solid. The chemical equation for this reaction is illustrated below and the properties of the obtained product are given below.

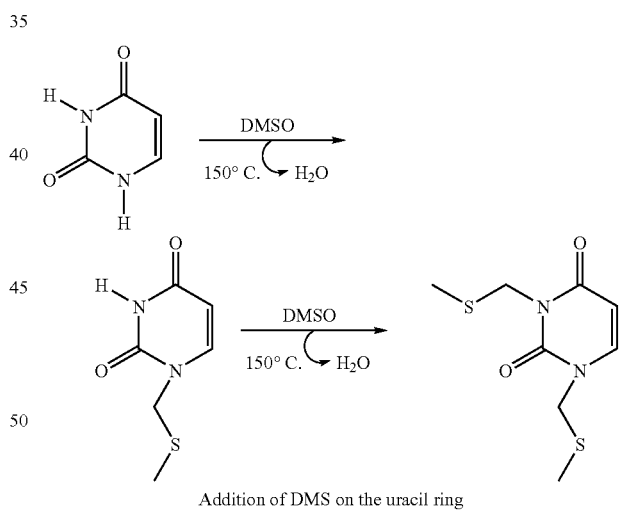

Addition of DMS on the uracil ring

Properties of 1,3-bis-(methylthiomethyl)uracil

| | |
|---|---|
| MP (° C.) | 68-70 |
| Molecular mass | 232.01 (EI) |
| IR (cm$^{-1}$) | 3085 (m), 3021 (m), 2924 (m), 1714 (s), 1662 (s), 1443 (s) 1353 (s), 825 (m), 774 (s), 542 (m), 510 (m) |
| $^1$H NMR (ppm) | 2.157 (3 H, s), 2.197 (3 H, s), 4.890 (2 H, s), 4.918 (2 H, s), 5.803-5.833 (1 H, d), 7.789-7.819 (1 H, d) |
| $^{13}$C NMR (ppm) | 15.143, 16.747, 44.663, 52.375, 101.634, 144.356, 151.451, 162.631 |

Synthesis of 5-hexynyluracil and 6-n-butylfuranopyrimidin-2-one 2.4 g of 5-iodouracil were mixed with 50.0 mL of anhydrous triethylamine (refluxed over calcium hydride and distilled) to yield a yellow slurry through which argon was bubbled for 15 minutes in order to deoxygenate the mixture. To the mixture, 50.0 mg of $(Ph_3P)_2PdCl_2$, 50.0 mg of copper (I) iodide and 2.0 g 1-hexyne were added; the reaction was allowed to proceed under Ar atmosphere in an oil bath set at 50° C. After 21 hours of reaction, TLC (EtOAc MeOH/Hexanes:5/1/2 by volume) indicated that some starting 5-iodouracil was still present in the reaction mixture, thus an extra 1.0 g of the 1-hexyne reagent was added, and complete disappearance of the starting reagent 5-iodouracil was observed. 3 hours later by TLC, which also, indicated that one of the reaction products was fluorescent under Ultraviolet (UV) light.

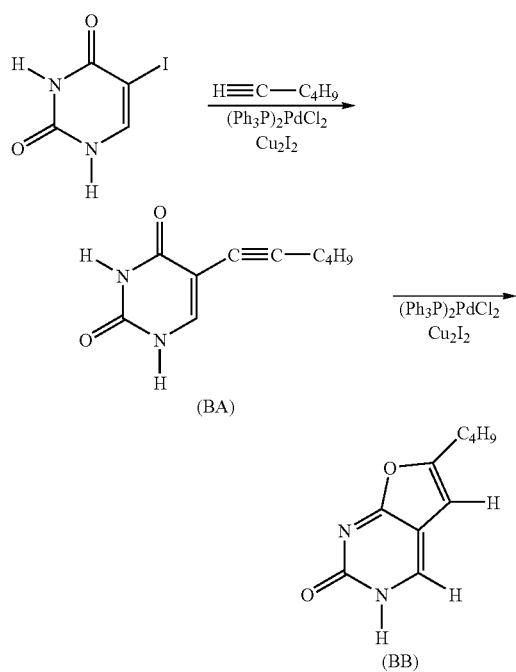

The 1-hexyne and 5-iodouracil coupling reactions

After consumption of the 5-iodouracil, the triethylamine was distilled off under reduced pressure to obtain a brownish yellow slurry to which 50.0 mL of EtOAc was added and then extracted twice with 50.0 mL of a 5% aqueous solution of the sodium salt of ethylenediaminetetraacetic acid (EDTA) and once with 50.0 mL of distilled water. This extraction resulted in a dark red organic layer and a green aqueous phase whose surface was covered with a white foam. TLC on these fractions revealed that the reaction products were present in both the foam and the organic layer, none was found in the liquid aqueous phase. The supernatant foaming substance was isolated by decanting off the aqueous phase and washed with water, filtered and air dried to obtain white solid that showed two different spots on TLC. The organic phase was completely distilled off to produce a brown-red oil from which reaction products were obtained by crystallization from ethyl acetate (EtOAc)/hexanes. These products were found to be identical to those from the foaming substance, as by TLC, and were all mixed prior to separation and purification.

Separation and Purification

TLC $R_f$ value evaluations in different organic solvents indicated that EtOAc was the most appropriate solvent for separation by crystallization as the $R_f$ was 0.553 between the fluorescent ($R_f$=0.027) and the non fluorescent ($R_f$=0.580) products.

Thus, 75.0 mL of EtOAc was added to the mixture of products and the resulting slurry was refluxed with stirring for 10 minutes, then cooled to 35° C. and filtered. The white solid was washed with cold EtOAc, air-dried and checked for purity by TLC, which revealed a single spot of the fluorescent product. The filtrate was concentrated on a rotary evaporator to approximately 50 mL and the separation process was repeated until the concentrated liquid phase contained no significant amount of the relatively insoluble fluorescent product. At this stage, the non-fluorescent product was separated from residual fluorescent product by running the solution through a silica gel column eluted with EtOAc. Although the first fractions contain only the non-fluorescent product and the fluorescent product is retained on the column. Collected fractions were evaporated to dryness and the resulting slurry was dissolved in a minimum volume of acetone and the product was precipitated with hexanes. After filtration, the product was washed with diethyl ether and dried overnight under high vacuum to obtain a white powder showing a single non-fluorescent spot on TLC under UV light and having the properties given below.

Observed Properties of Non-fluorescent (BA) and Fluorescent (BB) Products

|  | (BA) | (BB) |
|---|---|---|
| Yield | 431.3 mg (23.9%) | 1.3031 g (70.1%) |
| MP (° C.) | 238-241 | 264-266 |
| Molecular mass | 191.9 (EI) | 192.0 (EI) |
| IR (cm$^{-1}$) | 3227 (s, br), 3072 (s), 2963 (s), 2235 (m), 2023 (m), 1727 (s, br), 1624 (s), 1443 (s), 1328 (m), 1237 (s), 999 (w), 941 (m), 832 (s), 754 (s), 548 (s) | 3423 (w, br), 3123 (s), 3077 (s), 2949 (s), 1985 (w), 1838 (w), 1638 (s, br), 1578 (s), 1480 (s), 1405 (s), 1339 (s), 1174 (s), 1122 (s), 853 (s), 783 (s), 622 (m), 575 (s) |
| $^1$H NMR (ppm) | 0.885-0.909 (3 H, t), 1.333-1.508 (4 H, m), 2.323-2.368 (2 H, t), 7.634 (1 H, s), 11.136 (1 H, s), 11.261 (1 H, s) | 0.881-0.928 (3 H, t), 1.287-1.381 (2 H, m), 1.546-1.642 (2 H, m), 2.608-2.656 (2 H, t), 6.368 (1 H, s), 8.141 (1 H, s), 11.871 (1 H, s) |
| $^{13}$C NMR (ppm) | 14.3, 19.3, 22.2, 31.2, 73.8, 93.5, 98.5, 145.4, 151.3, 163.7 | 14.4, 22.4, 27.9, 29.3, 100.4, 106.8, 139.7, 156.7, 158.6, 172.9 |

Synthesis of 5-bromo-1-benzyluracil 5.3 g (47 mmols) of uracil and 2.65 g (47 mmols) of potassium hydroxide pellets were mixed with 20 mL of DMSO, and stirred at room temperature to form as white slurry which was stirred in an oil bath set at 65° C. until complete dissolution of the starting materials. To the resulting solution, 20 mL of 50% (v/v) benzylbromide solution in DMSO was added, and the reaction was allowed to proceed at 85° C. under an argon atmosphere for 72 hours. The course of the reaction was monitored by TLC using a solvent system made of EtOAc/methanol/hexanes:10/1/4 (by volume). Additional benzylbromide (2×5 mL) was required for total consumption of the starting uracil. After 72 hours of reaction, TLC indicated that all starting uracil had disappeared but some non-alkylated bromouracil was still present. The reaction was halted and the product was isolated following the procedure below:

At 75° C. under reduced pressure, DMSO was completely distilled off and to the resulting yellow slurry acetone was added to dissolve the reaction product and precipitate the potassium bromide. The inorganic salt was removed by filtration, and the resulting filtrate was evaporated to yield a thick oil which was then mixed with 40 mL of EtOAc, stirred well, and extracted with water (2×40 mL). TLC revealed that the unalkylated 5-bromouracil was in the aqueous layer while the targeted alkylated product was in the organic phase.

The organic layer was dried with sodium sulfate and filtered by gravity. The obtained filtrate was completely evaporated to an oil from which the crude pale yellow product was isolated by crystallization with ethyl acetate and hexane. This product was then recrystallized from acetone-water, washed with dichloromethane and air dried under high vacuum to yield pure white crystals whose properties are given below.

The aqueous phase was evaporated to dryness and the resulting solid was dissolved in 25.0 mL of hot methanol after vigorous stirring. To this solution, diethyl ether was added slowly to precipitate 5-bromouracil as a white solid. Then, the mixture was cooled to room temperature, and then placed in an ice bath. The product, 5-bromouracil, was filtered out, washed with diethyl ether, then cold water, and dried under high vacuum to yield pure white crystals having the properties given below.

Observed Properties for 1-benzyl-5-bromouracil and 5-bromouracil

|  | 1-benzyl-5-bromouracil | 5-bromouracil |
| --- | --- | --- |
| Yield | 7.8 g (58.9%) | 1.3 g (15.6%) |
| MP (° C.) | 202-204 | >300, decomposes |
| Molecular mass | 279.99-281.99 (EI) | 189.8-191.8 (EI) |
| IR (cm$^{-1}$) | 3346 (m), 3069 (s), 2830 (s), 1660 (s, br), 531 (s), 608 (s), 638 (s), 685 (s), 746 (s) | |
| $^1$H NMR (ppm) | 4.883 (2 H, s), 7.284-7.394 (5 H, m), 8.370 (1 H, s), 11.845 (1 H, s) | 7.893-7.913 (1 H, t)*, 11.234 (1 H, s), 11.516 (1 H, s) |
| $^{13}$C NMR (ppm) | 58.815, 103.227, 135.636, 135.879, 136.771, 144.625, 153.313, 158.489, 167.722 | 102.565, 150.345, 158.973, 168.251 |

*Proton split by the N-1 of the uracil ring, J = 3.0 Hz

It was observed that bromination occurs before alkylation and a large excess of the alkylbromide is required for alkylation to occur. This suggests that benzylbromide is consumed in side reactions such as the direct OH substitution to form benzyl alcohol or oxidation by DMSO to benzaldehyde that may undergo disproportionation:

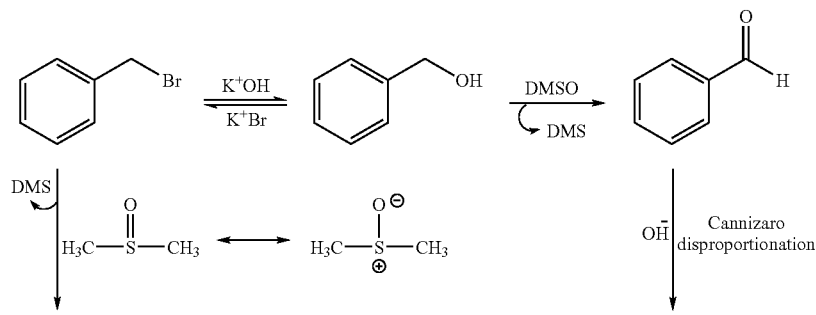

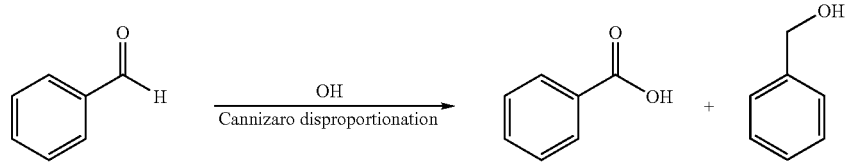

Side reactions of benzylbromide

Syntheses of Other 1-alkyl-5-bromouracils

Syntheses of these uracil analogs follow the same procedure as for 1-benzyl-5-bromouracil but the isolation and purification of the reaction products may vary with the nature of the alkyl group, which appears to be the determining factor for the solubility of the resulting uracil analog.

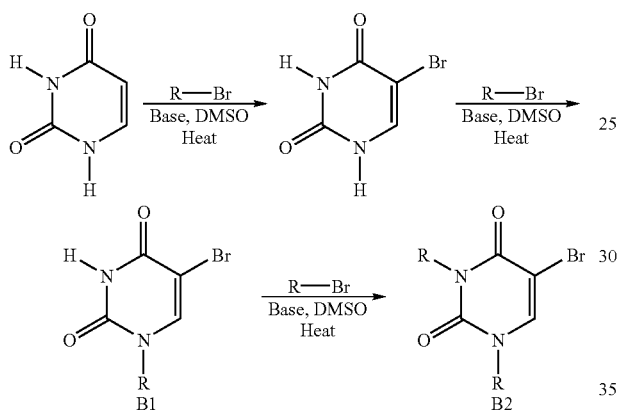

R = Alkyl groups (a)

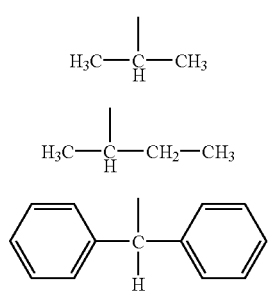

(b)

(c)

(d)

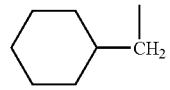

(e)

General Scheme for the Synthesis of N-alkyl-5-bromouracils

Synthesis of B1a

The same procedure as for 1-benzyl-5-bromouracil but the recrystallization was done from ethanol-water to yield 2.59 g of pure white crystals B1a from 2.2 g of uracil, i.e., 56.9% yield. Even after 72 hours of reaction, 5-bromouracil could still be detected by TLC, but no B2a product was detected at any time in the course of reaction.

Synthesis of B1b

The same procedure as above was used, but the crystallization was done from EtOAc-hexanes and then from acetone alone to produce 1.96 g of pure white crystals B1b from 1.2 g of uracil, i.e., 74.4% yield. After 72 hours of reaction, 5-bromouracil could still be detected, but no B2b product was detected at any time in the course of reaction. Observed properties of compounds B1a and B1b are given below.

Observed Properties for B1a and B1b

| | B1a | B1b |
|---|---|---|
| MP (° C.) | 206-208 | 182-185 |
| Molecular mass | 231.9-233.9 (EI) | 247.0-249.1 (CI) |
| IR (cm$^{-1}$) | 3438 (w), 3338 (w), 3169 (s), 3060 (s), 2815 (s), 2017 (w), 1669 (s, br), 1340 (m), 1436 (s), 1224 (s), 1063 (m), 863 (m), 780 (m), 644 (s), 554 (s), 444 (s) | 3420 (w), 3169 (m), 3028 (s), 2834 (s), 2377 (w), 2087 (w), 1696 (s), 1661 (s), 1608 (s), 1426 (s), 1337 (m), 1285 (s), 1253 (s), 1179 (m), 1117 (m), 1042 (m), 949 (m), 880 (m), 747 (m), 622 (m) |
| $^1$H NMR (ppm) | 1.257-1.280 (6 H, d), 4.609-4.659 (1 H, m), 8.195 (1 H, s), 11.708 (1 H, s) | 0.750-0.799 (3 H, t), 1.248-1.270 (3 H, d), 1.617-1.673 (2 H, m), 4.4 (1 H, m), 8.168 (1 H, s), 11.725 (1 H, s) |
| $^{13}$C NMR (ppm) | 28.699, 55.828, 103.336, 149.761, 158.219, 167.305 | 11.616, 19.989, 28.417, 54.370, 96.581, 142.858, 151.655, 160.255 |

Synthesis of B1d and B2d

The same procedure and reaction time as for the synthesis of 5-bromo-1-benzyluracil was used. However, after DMSO removal by distillation under reduced pressure, KBr precipitation and water-EtOAc extraction, the excess of p-nitrobenzylbromide was washed away with either leaving behind the reaction product mixture of B1d and B2d, as revealed by both TLC and proton NMR experiments.

Separation and Purification of B1d and B2d

Due to the poor solubility of these reaction products, separation by column chromatography was deemed impractical: thus, the compounds solubility differences in acetone was exploited for separation by crystallization as follows:

100.0 mL of acetone were added to the mixture to form a slurry that was refluxed for 10-15 minutes while stirring vigorously.

The mixture was allowed to slowly cool down to 35° C. and filtered by gravity.

The white solid was washed with cold acetone and dried overnight under high vacuum to yield the pure B2d product as revealed by TLC and later confirmed by NMR experiments. TLC on the filtrate revealed that it contained both B1d and B2d products.

This separation process was repeated as necessary until no significant amount of B2d was present in the filtrate. This is easily observable by the cloudiness of the acetone mixture, which decreases with the amount of the relatively insoluble B2d left in the mixture.

Observed Properties for the Reaction Product B2d

| MP (° C.) | 288-291 |
|---|---|
| Molecular mass | 461.1-463.1 (EI) |
| IR (cm$^{-1}$) | 3446 (w, br), 3118 (w), 3092 (w), 3027 (w), 2448 (w), 1804 (w), 1707 (s), 1662 (s), 1521 (s), 1430 (m), 1347 (s), 1205 (s), 1051 (s), 857 (m), 696 (s), 561 (s), 430 (m) |
| $^1$H NMR (ppm) | 5.100 (2 H, s), 5.130 (2 H, s), 7.519-7.635 (4 H, 2 d), 8.163 (4 H, 2 d), 8.584 (1 H, s) |
| $^{13}$C NMR (ppm) | 45.645, 52.632, 95.650, 124.423, 124.562, 129.412, 144.748, 145.158, 145.342, 147.593, 151.444, 159.803 |

Synthesis of B1e and B2e

The same procedure and reaction time as for the synthesis of 5-bromo-1-benzyluracil was used but the extraction was done in CHCl$_3$ and distilled water. The aqueous phase was discarded after TLC examination and the B1e and B2e reaction products were isolated from the organic phase as follows.

Using a rotary evaporator, the solvent was completely removed from the organic phase and the resulting brown slurry was dissolved in methanol. The product was then precipitated with diethyl ether, as a pale yellow solid. The liquid phase was decanted off and the product was recrystallized from MeOH and ether. After filtration, washing with diethyl ether to remove the yellow color, and drying overnight under high vacuum, a white powder that was found to correspond to compound B1e was produced. Its observed properties are given below. All the liquids collected from the organic phase treatment were mixed and evaporated to an oil. The resulting oil was dissolved in ethanol and the crude product was precipitated as an orange solid by adding distilled water to the ethanol solution. Recrystallization from ethanol alone afforded coarse yellow crystals B2e after filtration, washing with hexanes and drying overnight under high vacuum. Additional yellow product B2e was obtained from the filtrate after complete evaporation of the liquid phase to an oil and repetition of the last purification step. The properties of product B2e are shown below.

Observed Properties for the Reaction Product B1e and B2e

|  | B1e | B2e |
|---|---|---|
| Yield and (color) | 43.4% (white) | 6.3% (yellow) |
| MP (° C.) | 243-244 (decomposes) | 140-141 |
| Molecular mass | 287.2-289.2 (EI) | 384.4-386.4 (EI) |
| IR (cm$^{-1}$) | 3404 (w), 3154 (m), 3039 (s), 2923 (s), 2850 (s), 1701 (s), 1658 (s), 1622 (s), 1458 (s), 1433 (s) | 3411 (w), 3092 (w), 2923 (s), 2848 (s), 2666 (w), 1715 (s), 1658 (s), 1452 (s), 1326 (s) |
| $^1$H NMR (ppm) | 0.88-0.928 (2 H, m), 1.123-1.153 (3 H, m), 1.544-1.695 (6 H, m), 3.325-3.327 (1 H, d), 3.506-3.531 (2 H, d), 8.189-8.191 (1 H, d), 11.730 (1 H, s) | 0.907-0.944 (4 H, m, br), 1.123-1.147 (6 H, br), 1.498-1.685 (12 H, m, br), 3.325-3.327 (2 H, d), 3.573-3.597 (2 H, d), 3.691-3.715 (2 H, d), 8.258-8.260 (1 H, d) |
| $^{13}$C NMR (ppm) | 25.979, 26.705, 30.433, 37.413, 54.263, 95.194, 146.508, 151.340, 160.470 | 26.133, 26.723, 30.443, 31.068, 36.477, 37.422, 48.249, 55.401, 94.600, 145.084, 151.545, 159.816 |

Synthesis of 1-benzyluracil

This experiment was performed to verify the role of DMSO solvent in the generation of the bromine electrophile. Thus, this synthesis was done following the same procedure as for the synthesis of 1-benzyl-5-bromouracil, with the sole exception that DMSO was replaced by dimethylformamide (DMF), as solvent. Extraction was done by water-EtOAc and crystallization was done from EtOAc-Hexanes. After filtration, washing with hexanes and drying under high vacuum, 1.4 g of pure 1-benzyluracil, was isolated, as clean white crystals with properties shown below.

Observed Properties for 1-benzyluracil

| Yield | 64.7% |
|---|---|
| MP (° C.) | 178-179 |
| Molecular mass | 201.9 (EI) |
| IR (cm$^{-1}$) | 3418 (w, br), 3148 (s), 3057 (s), 3019 (s), 2884(m), 2813 (m), 2362 (w), 1672 (s, br), 1467 (s), 1345 (s), 1248 (s), 1203 (s), 958 (m), 894 (s), 733 (s), 521 (s) |
| $^1$H NMR (ppm) | 4.875 (2 H, s), 5.587-5.614 (1 H, d), 7.278-7.396 (5 H, m), 7.749-7.777 (1 H, d), 11.316 (1 H, br) |
| $^{13}$C NMR (ppm) | 51.096, 102.201, 128.276, 128.529, 129.527, 137.745 146.512, 151.884, 164.532 |

Synthesis of 1-benzyluracil-6-methyluracil

This experiment was undertaken after 6-methyluracil failed to yield the expected product, 1-benzyl-5-bromo-6-methyluracil, following the general procedure the synthesis of 5-bromo-1-benzyluracil, supra. Following this general procedure, 6-methyluracil underwent C-5 bromination but no alkylation product was detected even after 72 hours of reaction. When the solvent DMSO was replaced by DMF, N-1 alkylation occurred but not bromination was observed even after 72 hours of reaction. These experimental observations suggest that the combined inductive effects due to bromine on C-5 and steric hindrance caused by the bulkier methyl group at C-6 are enough to prevent N-1 alkylation:

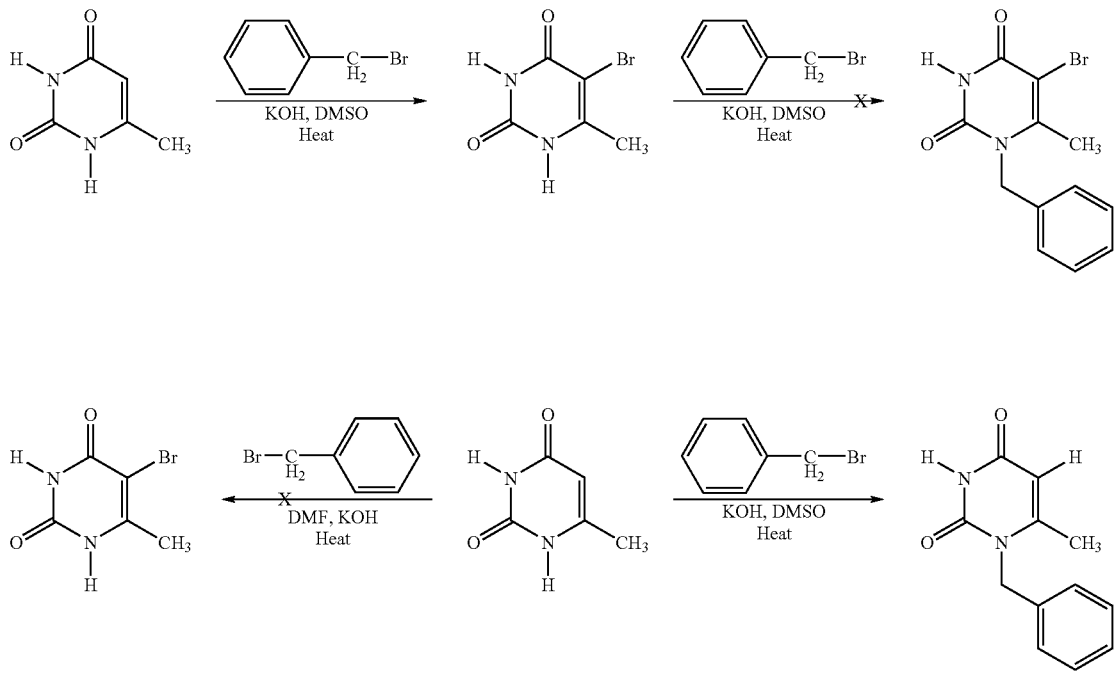

Solvent and Hinderance Effects on the General Reaction Outcomes

The synthesis of 1-benzyl-6-methyluracil followed the general procedure with the exception that DMSO was replaced by DMF, as the solvent. Extraction was performed in water-EtOAc and crystallization was done from EtOAc-hexanes. After purification and drying, 1.63 g of pure product was isolated as white crystals with properties given below.

Observed Properties for the Reaction Products 5-bromo-6-methyluracil and 1-benzyl-6-methyluracil

|  | 5-bromo-6-methylurcil | 1-benzyl-6-methyluracil |
|---|---|---|
| Yield (%) | 71.2 | 70.9 |
| MP (° C.) | 262-264 | 239-240 |
| Molecular mass | 204-206 (EI) | 216.1 (EI) |
| IR (cm$^{-1}$) | 3076 (s, br), 2826 (s), 2517 (m) 2420 (m), 2092 (w), 1665 (s, br), 1422 (s), 1313 (s), 1094 (s), 881 (s), 675 (s), 604 (s), 527 (s) | 3463 (w, br), 3141 (w), 3015 (m), 2787 (m), 1718 (s), 1660 (s), 1609 (s), 1480 (s), 1409 (s), 1351 (m), 1177(m), 1087 (m), 894 (m), 733 (m), 701 (m), 508 (m) |
| $^1$H NMR (ppm) | 2.20 (3 H, s), 11.30 (1 H, s), 11.42 (1 H, s) | 2.121 (3 H, s), 5.050 (2 H, s), 5.558 (1 H, s), 7.18-7.41 (5 H, m), 11.32 (1 H, s) |
| $^{13}$C NMR (ppm) | 27.588, 103.074, 158.333, 159.467, 168.081 | 20.086, 46.819, 102.286, 126.796, 128.116, 129.654, 137.936, 152.876, 155.160, 163.323 |

Synthesis of 1-benzyl-6-n-butylfuranopyrimidin-2-one

The synthesis of 5-hexynyluracil and 6-n-butylfuranopyrimidin-2-one has been described earlier. Benzylation of the synthesis reaction mixture prior to separation and purification of 5-hexynyluracil, 6-n-butylfuranopyrimidin-2-one, and residual starting 5-iodouracil led to formation of 1-benzyl-5-iodouracil, 1-benzyl-6-n-butylfuranopyridimidin-2-one and traces of 1-benzyl-5-hexynyluracil that contaminated the 1-benzyl-5-iodouracil product as revealed by TLC, Mass Spectrometry, and proton NMR. This suggests that the open chain substituent of (B2) cyclizes to yield the product (B3), which is thermodynamically favored. In fact, previous investigators (Robins M. J. and Barr P. J., Tetrahedron Lett., 1981, 22:421) had already observed this conversion for analogs substituted with sugar or methyl groups at the N-1 position of the uracil ring. The synthesis and purification of 1-benzyl-6-n-butylfuranopyrimidin-2-one and 1-benzyl-5-iodouracil were achieved following the procedure below.

As above, 5-hexynyluracil and 6-n-butylfuranopyrimidin-2-one was prepared from 3.0 g of 5-iodouracil and 3.0 mL of 1-hexyne at 50° C. for 24 hours. Triethylamine solvent was completely distilled off at reduced pressure and a pale yellow slurry was obtained. This slurry was dissolved in 50.0 mL of DMF containing 0.70 g of KOH, and the resulting dark red solution was heated in an oil bath at 65° C. for 10 minutes. Then, 3.0 mL of benzylbromide was added to the red solution and the reaction was allowed to proceed under an Ar atmosphere until complete benzylation of 6-n-butylfuranopyrimidin-2-one to yield 1-benzyl-6-n-butylfuranopyrimidin-2-one. This alkylation took approximately 9 hours and it was monitored by TLC, as both 6-n-butylfuranopyrimidin-2-one and 1-benzyl-6-n-butylfuranopyrimidin-2-one are fluorescent under UV light but have significantly different $R_f$ values in various solvent systems including EtOAc MeOH/Hexanes: 10/1/4 and EtOAc/Ether:2/1. Once the alkylation was complete, DMF solvent was distilled off under reduced pressure and 50.0 mL of dry acetone was added to the resulting slurry to precipitate potassium bromide that was removed by gravity filtration. The filtrate was evaporated to a dark red viscous oil that was dissolved in 40.0 mL of chloroform and extraction was performed with 5% aqueous solution of EDTA (sodium salt) 2×40.0 mL and then once with 40.0 mL of distilled water.

The organic phase was completely evaporated to a dark red oil which was dissolved in acetone and the resulting solution was treated with activated charcoal, as an attempt to remove impurities that colored the products. Separation by column chromatography on silica gel flushed with EtOAc/Hexanes: 5/1 (by volume) produced pure 1-benzyl-6-n-butylfuranopyrimidin-2-one and 1-benzyl-5-iodouracil contaminated with traces of 1-benzyl-5-hexynyluracil. The properties for 1-benzyl-6-n-butylfuranopyrimidin-2-one and 1-benzyl-5-iodouracil are given below. However, the other product 1-benzyl-5-hexynyluracil could not be isolated or purified in sufficient amount for structural determination, thus, its properties are not available. The reaction final products, 1-benzyl-6-n-butylfuranopyrimidin-2-one and 1-benzyl-5-iodouracil, were purified and recrystallized from $CHCl_3$/hexanes. After filtration, the isolated products were washed with cold ether and dried under a high vacuum to yield pure products in the form of crystals having the properties given below.

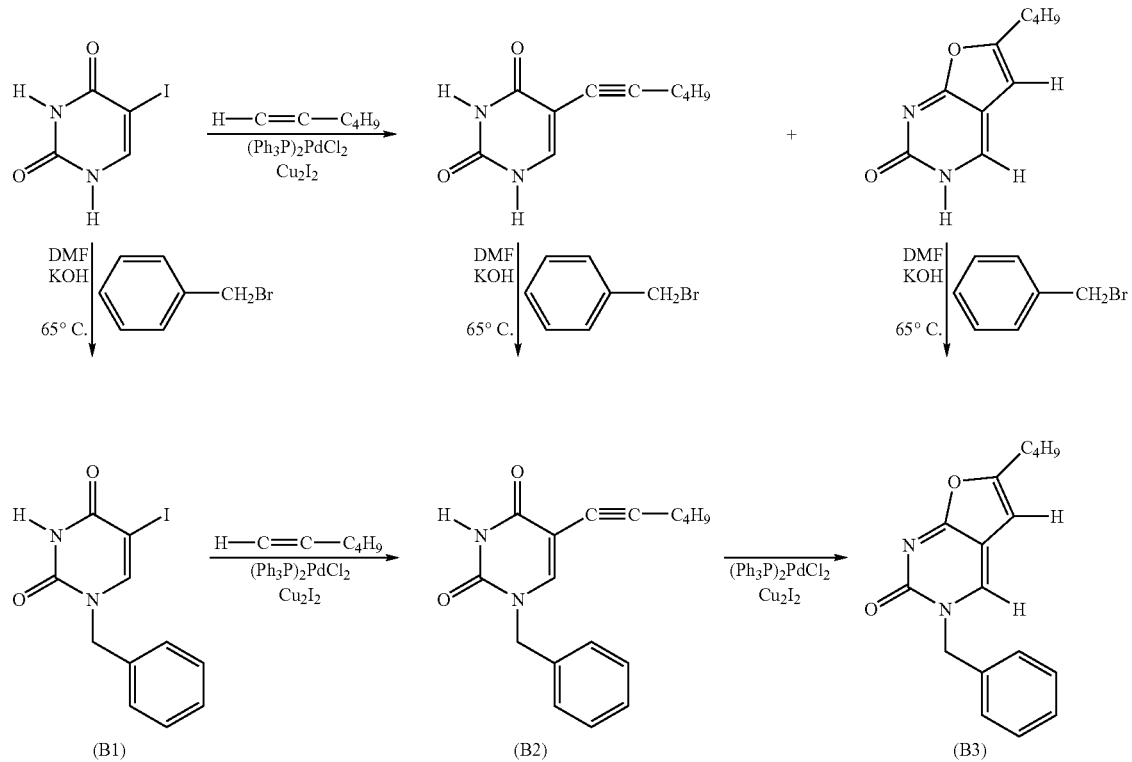

The Synthesis of
1-benzyl-6-n-butylfuranopyrimidin-2-one and
1-benzyl-5-iodouracil Observed Properties of the Reaction Products 1-benzyl-5-iodouracil (B1) and 1-benzyl-6-n-butylfuranopyrimidin-2-one (B3)

|  | (B1) | (B3) |
|---|---|---|
| MP (° C.) | 210-213 | 196-198 |
| Molecular mass | 328.0 (346.1 = M + NH$_4$) (CI) | 282.2 (EI) |
| IR (cm$^{-1}$) | 3431 (w, br), 3161 (m), 3122 (m), 3083 (m), 2839 (m), 2491 (w), 2375 (w), 1725 (s), 1680 (s), 1615 (s), 1499 (m), 1461 (s), 1428 (s), 1345 (s), 1242 (m), 1145 (m), 917 (m), 887 (m), 733 (s), 701 (m), 527 (m) | 3457 (w, br), 2967 (m), 2942 (m), 2871 (m), 1680 (s), 1641 (s), 1570 (s), 1454 (m), 1422 (s), 1377 (s), 1338 (m), 1242 (m), 1139 (m), 1068 (m), 933 (m), 830 (m), 778 (m), 701 (s), 611 (m), 546 (m) |
| $^1$H NMR (ppm) | 4.879 (2 H, s), 7.280-7.392 (5 H, m), 8.348 (1 H, s), 11.714 (1 H, s) | 0.877-0.925 (3 H, d), 1.308-1.382 (2 H, m), 1.571-1.621 (2 H, m), 2.616-2.666 (2 H, t), 5.146 (2 H, s), 6.438 (1 H, s), 7.288-7.346 (5 H, m), 8.6000 (1 H, s) |
| $^{13}$C NMR (ppm) | 51.354, 69.566, 128.368, 128.607, 129.524, 137.550, 150.631, 151.602, 161.896 | 14.42, 22.36, 27.90, 29.29, 54.19, 100.33, 107.54, 128.55, 128.60, 129.43, 137.66, 142.65, 155.42, 159.20, 172.28 |

Biological Testing

Potential drug-molecules can be tested in a variety of seizure models. These models include pilocarpine induced-seizures (PIS) model, the spontaneous recurrent seizure (SRS) model, maximal electroshock induced-seizures (MES), subcutaneous pentylenetetrazole induced-seizures (PTZ) model and the hippocampal kindling seizure model. Most of test compounds P1-P 43 showed some activity in at least one of these assays.

Pilocarpine Induced-seizure (PIS) Model

All test compounds are normally dissolved in a mixture of saline (NaCl 0.9% by mass) and 10% DMSO. However, in case of solubility problems, the concentration of DMSO may be increased to a maximum of 50%. This biological test is performed following the procedure disclosed in PCT publication WO 98/40055 (Queen's University at Kingston).

Spontaneous Recurrent Seizure (SRS) Model

This model evaluates the anti-epileptogenic activity of test compounds. The biological test is done according to the procedure illustrated below and the test compound is dissolved in saline/DMSO as in the PIS test. The "spontaneous recurrent seizures" (SRS) model of epilepsy is described in, e.g., Mello, E. et al., *Epilepsia* (1993) 34:985; Cavalheiro, J. et al., *Epilepsia* (1991) 32:778.

Maximal Electroshock Induced-seizure (MES) Model

The MES model is described in, e.g., "Molecular and Cellular Targets for Anti-Epileptic Drugs" G. Avanzini, et al. (1997) John Libbey & Company Ltd., pp 191-198; Chapter 16, "The NIH Anticonvulsant Drug Development (ADD) Program: preclinical anticonvulsant screening project," by James P. Stables and Harvey J. Kupferberg.

Subcutaneous Pentylenetetrazole Induced-seizure (PTZ) Model

In this test, the convulsant dose of pentylenetetrazole (85 mg/kg in mice and 70 mg/kg in rats) is injected at the time of peak effect of the test compound. Then, the animals are isolated and observed for a period of 30 minutes to see if seizures occur. Absence of clonic spasms persisting for five seconds or longer is an indication that the test compound may have the ability to increase the pentylenetetrazole induced-seizure threshold.

Hippocampal Kindling Seizure Model

This model is particularly useful as it, not only, provides an experimental model of seizures but also offers a means of studying the complex brain networks that may contribute to the spread and generalization of seizures from the focus. Biological testing using hippocampal kindling seizure model follows the Lothman procedure (Lothman, et al., *Epilepsy Res.*, 1988, 2:366) or the Silver procedure (Silver, et al., *Ann. Neurol.* (1991) 29:356). See also, Lothman, et al., *Brain Res.*, 1994, 649:71, and Racine, et al., *Clin. Neurophysiol.*, 1972, 32:281.

Neurotoxicity Screen

Preliminary neurotoxicity induced by the test compound may be characterized by neurologic abnormalities and poor performances in given tasks. For instance, the neurologic deficit may be indicated by the inability to maintain equilibrium for one minute in each of three trials on a knurled rod rotating at 6 rpm. Other tests for neurotoxicity include the rotorod ataxia test, positional sense test, and gait and stance test. In the positional sense test, one hind leg is gently lowered over the edge of a table. The animal quickly reacts by returning the leg to the normal position. Failure to do so rapidly, indicates a neurologic deficit. In the gait and stance test, the neurologic deficit is indicated by a circular or zigzag gait, ataxia, and other abnormal events that may include abnormal spread of legs, body posture, tremor, hyperactivity, lack of exploratory behavior, somnolence, stupor, and catalepsy.

Initial testings (PTZ, MES, Neurotoxicity) were carried out in 12 animals at doses of 30, 100, 300 mg/kg i.e. 4 animals per test, at interval times of 30 minutes and 4 hours after administering the test compound.

Biological Testing Results

The compounds evaluated for biological activity are presented with their structural formulas and reference numbers below; their in vivo biological test results are given in Table A.

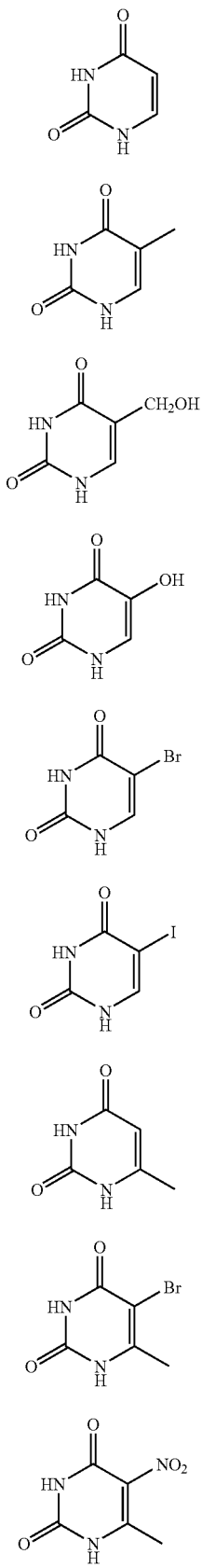

-continued
(P18)
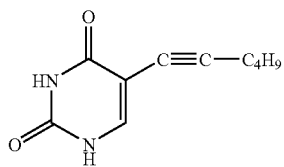
(P19)
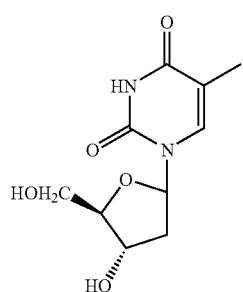
(P20)
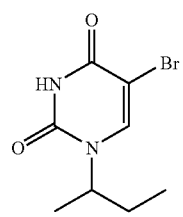
(P21)
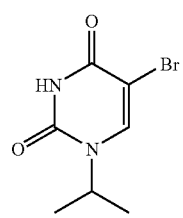
(P22)
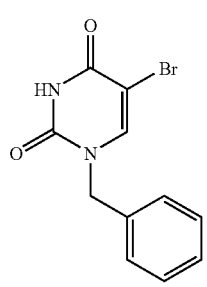
(P23)
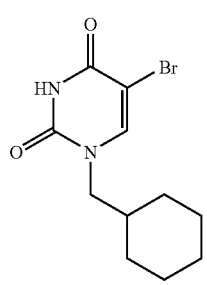
-continued
(P24)
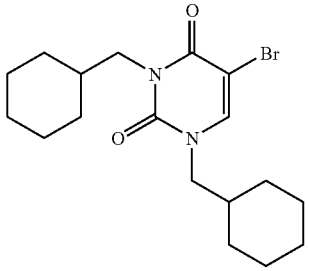
(P25)
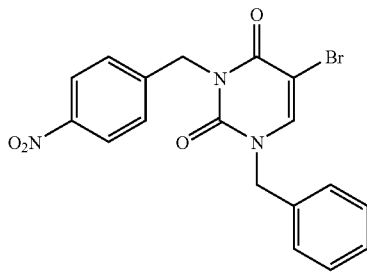
(P26)
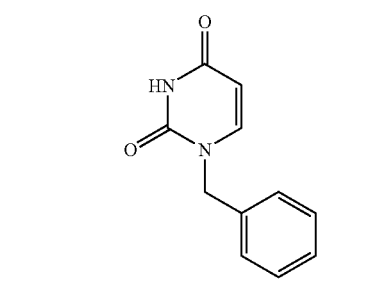
(P27)
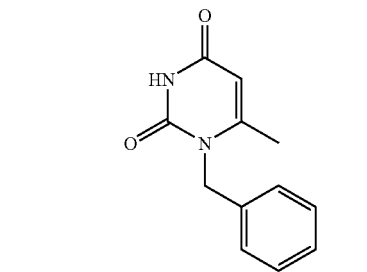
Other anti-ictogenic and/or anti-epileptogenic pyrimidine compounds in accordance with the invention include:
(P28)
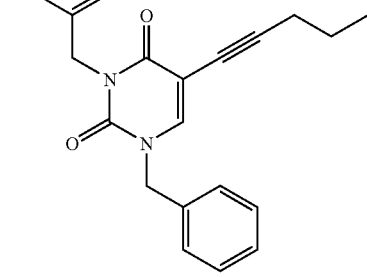

-continued
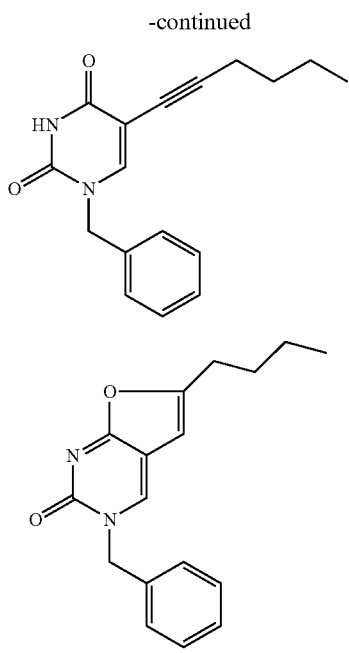
(P29)
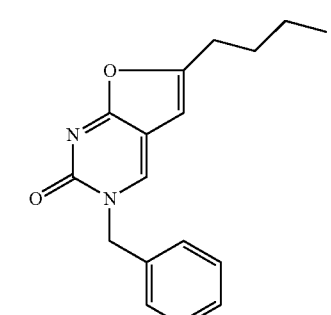
(P30)
Further anti-ictogenic and/or anti-epileptogenic pyrimidine compounds in accordance with Formula XIV of the present invention include:
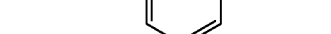
(P31)
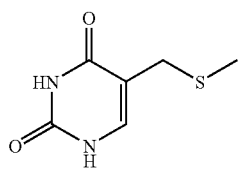
(P32)
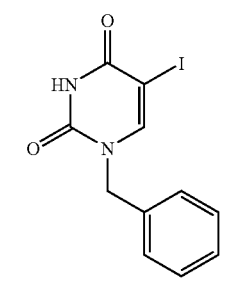
(P33)
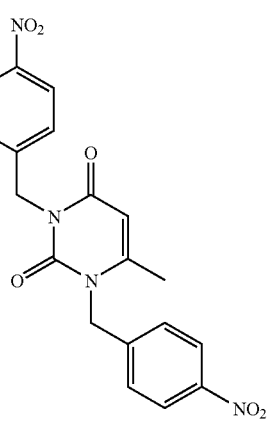
-continued
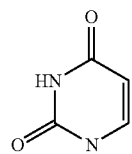
(P34)
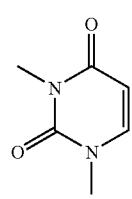
(P35)
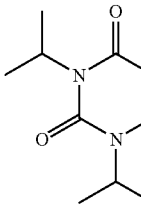
(P36)
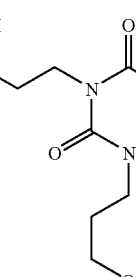
(P37)
Further examples of active compounds according to Formula XIV include the following:
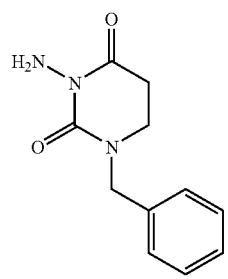
(P38)
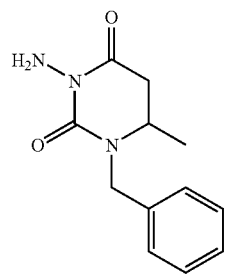
(P39)

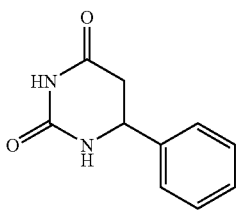
(P40)

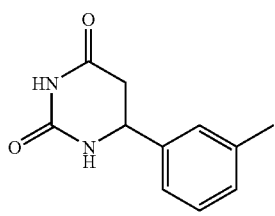
(P41)

Still further examples of active compounds according to the invention include

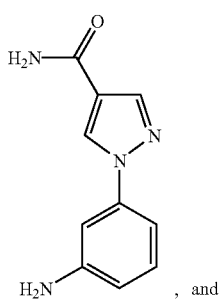
, and
(P42)

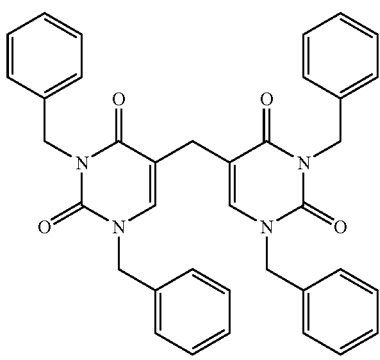
(P43)

TABLE A

Biological test results of uracils in the Pilocarpine model

| Compound Reference # | Relative Activity (Maximum = 4) |
|---|---|
| P1 | Active - +2 |
| P2 | Active - +2 |

TABLE A-continued

Biological test results of uracils in the Pilocarpine model

| Compound Reference # | Relative Activity (Maximum = 4) |
|---|---|
| P3 | Active - +3 |
| P4 | Active - +2 |
| P5 | Active - +1 |
| P6 | Active - +1 |
| P7 | Active - +3 |
| P8 | Active - +2 |
| P9 | Active - +2 |
| P10 | Minimally Active |
| P11 | Active - +2 |
| P12 | Active - +2 |
| P13 | Minimally Active |
| P14 | Active - +2 |
| P15 | Minimally Active |
| P17 | Active - +1 |
| P18 | Active - +1 |
| P19 | Minimally Active |
| P20 | Active - +1 |
| P21 | Active - +1 |
| P22 | Active - +1 |
| P23 | Minimally Active |
| P24 | Minimally Active |
| P25 | Active - +2 |
| P26 | Active - +2 |
| P27 | Active - +2 |
| P28 | NA |
| P29 | NA |
| P30 | NA |
| P31 | Minimally Active |
| P32 | Active +1 |
| P33 | Active +2 |
| P34 | Minimally Active |
| P35 | Active +3 |
| P36 | Active +2 |
| P37 | Active +2 |
| P38 | Active +2 |
| P39 | Active +3 |
| P40 | NA |
| P41 | NA |
| P42 | Active +2 |
| P43 | Active +3 |

("NA" = not available)

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, issued patents, and published patent applications cited throughout this application are hereby incorporated by reference. The appropriate components, processes, and methods of those patents, applications and other documents may be selected for the present invention and embodiments thereof.

What is claimed is:

1. A method of treating ictogenesis or seizures in a subject in need thereof comprising administering to said subject a pharmaceutical composition comprising an effective amount of a compound and a pharmaceutically acceptable carrier, wherein the compound is selected from the group consisting of

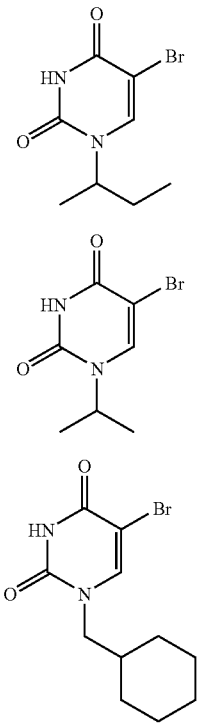

(P20)

(P21)

(P23)

and pharmaceutically acceptable salts or esters thereof.

2. The method of treating ictogenesis or seizures accordingly to claim 1, wherein the compound is (P20) or a pharmaceutically acceptable salt or ester thereof.

3. The method of treating ictogenesis or seizures accordingly to claim 1, wherein the compound is (P21) or a pharmaceutically acceptable salt or ester thereof.

4. The method of treating ictogenesis or seizures accordingly to claim 1, wherein the compound is (P23) or a pharmaceutically acceptable salt or ester thereof.

5. The method of treating ictogenesis or seizures accordingly to claim 1, wherein said pharmaceutical composition is administered to said subject orally.

6. A method of treating epileptogenesis in a subject in need thereof comprising administering to said subject a pharmaceutical composition comprising an effective amount of a compound and a pharmaceutically acceptable carrier, wherein the compound is selected from the group consisting of

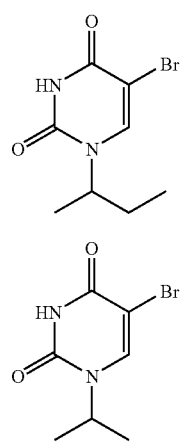

(P20)

(P21)

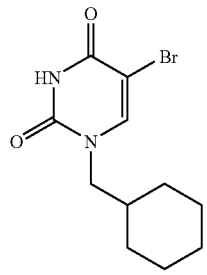

(P23)

and pharmaceutically acceptable salts or esters thereof.

7. The method of treating epileptogenesis accordingly to claim 6, wherein the compound is (P20) or a pharmaceutically acceptable salt or ester thereof.

8. The method of treating epileptogenesis accordingly to claim 6, wherein the compound is (P21) or a pharmaceutically acceptable salt or ester thereof.

9. The method of treating epileptogenesis accordingly to claim 6, wherein the compound is (P23) or a pharmaceutically acceptable salt or ester thereof.

10. The method of treating epileptogenesis accordingly to claim 6, wherein said pharmaceutical composition is administered to said subject orally.

11. The method of claim 1, wherein the seizures are caused by epilepsy.

12. A method of treating ictogenesis or seizures in a subject in need thereof comprising administering to said subject a pharmaceutical composition comprising an effective amount of a compound and a pharmaceutically acceptable carrier, wherein the compound is

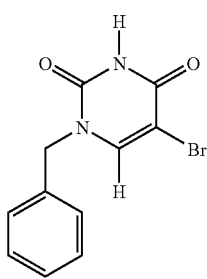

(P22)

or a pharmaceutically acceptable salt or ester thereof.

13. The method of treating ictogenesis or seizures accordingly to claim 12, wherein said pharmaceutical composition is administered to said subject orally.

14. A method of treating epileptogenesis in a subject in need thereof comprising administering to said subject a pharmaceutical composition comprising an effective amount of a compound and a pharmaceutically acceptable carrier, wherein the compound is

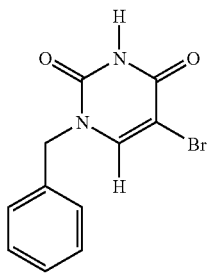

(P22)

or a pharmaceutically acceptable salt or ester thereof.

15. The method of treating epileptogenesis accordingly to claim 14, wherein said pharmaceutical composition is administered to said subject orally.

16. The method of claim 12, wherein the seizures are caused by epilepsy.

* * * * *